United States Patent
Pakula et al.

(10) Patent No.: US 9,512,415 B2
(45) Date of Patent: Dec. 6, 2016

(54) METHOD FOR PROTEIN PRODUCTION IN FILAMENTOUS FUNGI

(75) Inventors: Tiina Pakula, Espoo (FI); Markku Saloheimo, Espoo (FI); Mari Hakkinen, Espoo (FI); Ann Westerholm-Parvinen, Espoo (FI); Merja Penttila, Espoo (FI); Marika Vitikainen, Espoo (FI)

(73) Assignee: TEKNOLOGIAN TUTKIMUSKESKUS VTT Oy, Espoo (FI)

( * ) Notice: Subject to any disclaimer, the term of this patent is extended or adjusted under 35 U.S.C. 154(b) by 595 days.

(21) Appl. No.: 13/701,894

(22) PCT Filed: May 30, 2011

(86) PCT No.: PCT/FI2011/050492
§ 371 (c)(1),
(2), (4) Date: Dec. 14, 2012

(87) PCT Pub. No.: WO2011/151512
PCT Pub. Date: Dec. 8, 2011

(65) Prior Publication Data
US 2013/0078674 A1    Mar. 28, 2013

(30) Foreign Application Priority Data

Jun. 4, 2010 (FI) .................................. 20105632
May 30, 2011 (WO) .......................... FI2011/050492

(51) Int. Cl.
| | |
|---|---|
| C12P 21/02 | (2006.01) |
| C12N 9/48 | (2006.01) |
| C07K 14/37 | (2006.01) |
| C12N 15/80 | (2006.01) |
| C12N 9/00 | (2006.01) |
| C12N 9/16 | (2006.01) |
| C12N 9/24 | (2006.01) |
| C12N 9/42 | (2006.01) |
| C12P 21/00 | (2006.01) |

(52) U.S. Cl.
CPC ................ *C12N 9/48* (2013.01); *C07K 14/37* (2013.01); *C12N 9/00* (2013.01); *C12N 9/16* (2013.01); *C12N 9/2402* (2013.01); *C12N 9/244* (2013.01); *C12N 9/2437* (2013.01); *C12N 9/2477* (2013.01); *C12N 15/80* (2013.01); *C12P 21/00* (2013.01); *C12Y 302/01004* (2013.01); *C12Y 302/01006* (2013.01); *C12Y 302/01091* (2013.01); *Y02P 20/52* (2015.11)

(58) Field of Classification Search
None
See application file for complete search history.

(56) References Cited

U.S. PATENT DOCUMENTS

| | | |
|---|---|---|
| 2004/0186070 A1 | 9/2004 | Penttila et al. |
| 2011/0045526 A1* | 2/2011 | Bodie et al. .................... 435/34 |
| 2014/0004564 A1* | 1/2014 | Bodie et al. ................ 435/69.1 |

FOREIGN PATENT DOCUMENTS

WO    WO2010 034686 A1    4/2010

OTHER PUBLICATIONS

Aro, Nina; Transcriptional regulation of plant cell wall degradation by filamentous fungi; FEMS Microbiology Reviews vol. 29 No. 4; (2005) pp. 719-739.
Kubicek, Christian P., et al; Metabolic engineering strategies for the improvement of cellulase production by Hypocrea jecorina; Biotechnology for Biofuels; Sep. 2009, vol. 2, No. 1, p. 19.
Foreman, Pamela K., et al; Transcriptional Regulation of Biomass-degrading Enzymes in the Filamentous Fungus *Trichoderma reesei*\*; The Journal of Biological Chemistry; vol. 278. No. 34, Issue of Aug. 22, 2003; pp. 31988-31997.
Diener, S.E., et al; Characterization of the protein processing and secretion pathways in a comprehensive set of expressed sequence tags from Trichoderna reesei; FEMS Microbiology Letters; vol. 230, No. 2 (2004) 275-282.
Nakari-Setala, Tiina; Genetic Modification of Carbon Catabolite Repression in Trichoderma reesei for Improved Protein Production; Applied and Environmental Microbiology, Jul. 2009, vol. 75; p. 4853-4860.
Valkonen, Mari; et al; Improvement of Foreign-Protein Production in *Aspergillus niger* var. awamori by Constitutive Induction of the Unfolded-Protein Response; Applied and Environmental Microbiology,. vol. 69, No. 12; Dec. 2003, p. 6979-6986.
PCT/FI2011/050492; International Search Report & Written Opinion; Nov. 14, 2011.

\* cited by examiner

*Primary Examiner* — Jim Ketter
(74) *Attorney, Agent, or Firm* — Berggren, Inc.

(57) ABSTRACT

The present invention relates to a method for genetically modifying a filamentous fungus host for improved protein production. The method comprises that a filamentous fungus host is genetically modified to overexpress or to be deficient of specific genes. The invention relates also to the modified hosts. Furthermore, the invention relates to a method for improved production or for producing an improved composition of proteins, such as cellulases, hemicellulases, other proteins involved in the degradation of lignocellulosic material, or other proteins, in a filamentous fungus host.

11 Claims, 33 Drawing Sheets

SEQ ID NO:1
Strain15-5

SEQ ID NO:1
Strain15-5

SEQ ID NO:1
Strain15-5

SEQ ID NO:1
Strain15-5

SEQ ID NO:1
Strain15-5

SEQ ID NO:1
Strain15-5

SEQ ID NO:2
Strain 20-2

SEQ ID NO:2
Strain 20-2

SEQ ID NO:2
Strain 20-2

SEQ ID NO:2
Strain 20-2

SEQ ID NO:2
Strain 20-2

SEQ ID NO:2
Strain 20-2

SEQ ID NO:3
Strain 23-5

SEQ ID NO:3
Strain 23-5

SEQ ID NO:3
Strain 23-5

SEQ ID NO:3
Strain 23-5

SEQ ID NO:3
Strain 23-5

SEQ ID NO:3
Strain 23-5

SEQ ID NO:4
Strain 25-7

SEQ ID NO:4
Strain 25-7

SEQ ID NO:4
Strain 25-7

SEQ ID NO:4
Strain 25-7

SEQ ID NO:4
Strain 25-7

SEQ ID NO:4
Strain 25-7

SEQ ID NO:5
Strain 36-22

SEQ ID NO:5
Strain 36-22

SEQ ID NO:5
Strain 36-22

SEQ ID NO:5
Strain 36-22

SEQ ID NO:5
Strain 36-22

SEQ ID NO:5
Strain 36-22

METHOD FOR PROTEIN PRODUCTION IN FILAMENTOUS FUNGI

FIELD OF THE INVENTION

The present invention relates to a method for genetically modifying a filamentous fungus host for improved protein production. The invention relates also to providing a genetically modified filamentous fungus host for improved protein production, in particular a *Trichoderma* host. Furthermore, the present invention relates to a method for improved protein production or for producing an improved composition of proteins in filamentous fungi. The proteins may be endogenous proteins, such as hydrolytic enzymes, or heterologous proteins.

BACKGROUND OF THE INVENTION

Many of the biopolymer degrading hydrolytic enzymes, such as cellulases, hemicellulases, ligninases and pectinases have received attention because of their potential applications in food, feed, textile, and pulp and paper industries. Industrial filamentous fungi production strains, in particular *Aspergillus* and *Trichoderma* strains, can produce high amounts of extracellular enzymes. These fungi are easy and inexpensive to grow in large bioreactors and they possess good secretion capacity capable of carrying out similar type of protein modifications as occurs in many higher eukaryotes. The existence of hypersecreting strains and strong promoters, such as cellulase promoters, make filamentous fungi hosts also potential for heterologous protein production.

It is known that the production of cellulases, hemicellulases, ligninases and pectinases are mainly regulated at the transcriptional level in filamentous fungi (Aro et al. FEMS Microbiology Reviews 29 (2005) 719-739). Stricker et al. Appl. Microbiol. Biotechnol. (2208) 78:211-220 have described the similarities and differences in the transcriptional regulation of expression of hemicellulases and cellulases in *Aspergillus niger* and *Hypocrea jecorina* (*T. reesei*), including the action of XlnR and Xyr1. In *Hypocrea jecorina* some regulatory components function in cellulase regulation positively (XYRI, ACE2, HAP2/3/5) and some negatively (ACEI, CREI) (Kubicek et al. Biotechnology and Biofuels 2009, 2:19; Nakari-Setälä et al. Appl and Environmental Microbiology, July 2009, p. 4853-4860).

Although the action of some regulatory genes on the production of cellulases and hemicellulases has been disclosed in the prior art, there is still a need for improved strains capable of enhanced or altered production of cellulases or hemicellulases or other hydrolytic enzymes in filamentous fungi.

SUMMARY OF THE INVENTION

One object of the invention is to provide a method for genetically modifying filamentous fungus hosts for improved protein production.

Another object of the present invention is to provide genetically modified filamentous fungus hosts for improved protein production.

One further object of the invention is to provide a method for improved protein production or for producing improved composition of proteins in filamentous fungi.

In one aspect the invention provides a method for genetically modifying a filamentous fungus host for improved protein production. The method comprises genetically modifying a filamentous fungus host to overexpress (with increased amount or activity) genes causing increased production of cellulases, hemicellulases, other proteins involved in degradation of lignocellulosic material and/or other proteins;

and/or genetically modifying a filamentous fungus host by making deficient (with reduced or lacking amount or with reduced or lacking activity) genes causing increased production of cellulases, hemicellulases, other proteins involved in degradation of lignocellulosic material and/ or other proteins.

In a filamentous fungus host one or more of the genes causing increased production of cellulases, hemicellulases, other proteins involved in degradation of lignocellulosic material and/or other proteins can be genetically modified alone or in combination.

In one aspect the invention provides a method for increasing the production of a set of proteins, typically secreted proteins, or proteins produced under the control of promoters of genes encoding secreted proteins.

In another aspect the invention provides a method for reducing the production of a set of proteins, typically secreted proteins, in order to modify the pattern of produced proteins or reduction of the production of unwanted side-products when producing e.g. heterologous proteins.

One or more of the genes causing increased production of cellulases, hemicellulases, other proteins involved in degradation of lignocellulosic material and/or other proteins can be genetically modified alone or in combination in a filamentous fungus host.

In various embodiments of the invention the host can be selected from the group comprising *Trichoderma, Aspergillus, Fusarium, Neurospora, Talaromyces, Phanerochaete, Chrysosporium* and *Penicillium*. In one specific embodiment the filamentous fungus host is a *Trichoderma* host.

In one aspect of the invention the overexpressed gene causes increased production of cellulases, hemicellulases, other proteins involved in degradation of lignocellulosic material and/or other proteins, typically secreted proteins or proteins produced using the promoters of genes encoding secreted proteins as compared to the parent host. The increased production by the genetically modified hosts may be detected either as higher maximal production level during the cultivation as compared to the production level of the parental host or by higher production level at any of time points of the cultivation resulting in faster production process as compared to the parental host.

In one embodiment of the invention the overexpressed gene may be selected from the group comprising *Trichoderma* genes tre77513 (SEQ ID NO:1), tre80291 (SEQ ID NO:2), tre41573 (SEQ ID NO:3), tre74765 (SEQ ID NO:4), tre64608 (SEQ ID NO:5), or is the closest homologue of at least one of said genes in *Aspergillus, Fusarium, Neurospora, Talaromyces, Phanerochaete, Chrysosporium* or *Penicillium*; or a fragment or derivative of any of said genes or other sequence hybridizing under stringent conditions to at least one of said genes or said homologues. The overexpression of these genes causes increased production of, proteins, typically secreted proteins and/or proteins produced under the promoters of genes encoding secreted proteins, proteins involved in degradation of lignocellulosic material, in particular cellulases and/or hemicellulases as compared to the parental host.

In various embodiments of the invention filamentous fungi hosts can be constructed overexpressing a specific gene or a combination of specific genes, or being deficient of a specific gene or a combination of specific genes, or modified otherwise to alter the amount or activity of the protein product of the gene. In further embodiments, filamentous fungus hosts may be constructed overexpressing a specific gene or a combination of specific genes, and at the same time being deficient of a specific gene or a combination of specific genes.

In one further aspect the invention provides a method for improved production or production of improved composition of proteins in a filamentous fungus host, which comprises genetically modifying a filamentous fungus host as described above, and growing (cultivating) the modified filamentous fungus host under suitable culture conditions for protein production.

In one embodiment of the invention, the produced protein product may be an endogenous enzyme. Examples of suitable enzymes are hydrolytic enzymes, in particular cellulases, hemicellulases, cellulose or hemicellulose side chain cleaving enzymes, lignocellulose degrading enzymes, in particular pectinases and ligninases; amylolytic enzymes; proteases; invertases; phytases, phosphatases and hydrophobins.

In another embodiment of the invention, the protein is a heterologous protein produced under the regulation of the promoter of a gene that is affected by the genetical modification of the host, such as cellulase or hemicellulase promoter.

In one still further aspect the invention provides a genetically modified filamentous fungus host.

The host may be selected from the group comprising *Trichoderma, Aspergillus, Fusarium, Neurospora, Talaromyces, Phanerochaete, Chrysosporium* and *Penicillium*. More specifically the host may be a *Trichoderma* host.

By genetically modifying the regulatory genes or their regulatory mechanisms it is possible to improve the production of extracellular proteins in general, or the production of different sets of proteins and enzymes produced by filamentous fungi, in particular *Trichoderma*. These genetic modifications can be applied also to improve production of heterologous proteins when promoters and/or regulatory elements of genes encoding secreted proteins are used for the heterologous expression. The fungus host can be genetically modified to express the regulatory gene more or less abundantly or to produce more or less active regulatory protein from the gene. The genetic modification can include overexpression, deletion or any other genetic modification to alter expression strength of the gene or the activity of the product of the gene. The genetical modifications result in a desired effect on the produced protein pattern by the fungal production host. It may be beneficial to genetifically modify the production hosts in such a way that production of unwanted side products is reduced, or in such a way that a selected protein or a set of proteins are more abundantly expressed and other proteins produced less abundantly. Corresponding genetic modifications can be done also in other filamentous fungi, in order to modify protein production properties of the host, by modifying the corresponding homologous genes. In addition the corresponding genes from other fungal species can be introduced, as such or in a modified form, to other fungal species to get the desired effect on protein production in the other organism.

In the following text, the invention will be further described with the aid of a detailed description and with reference to some working examples.

DETAILED DESCRIPTION OF THE INVENTION

Figure 1:
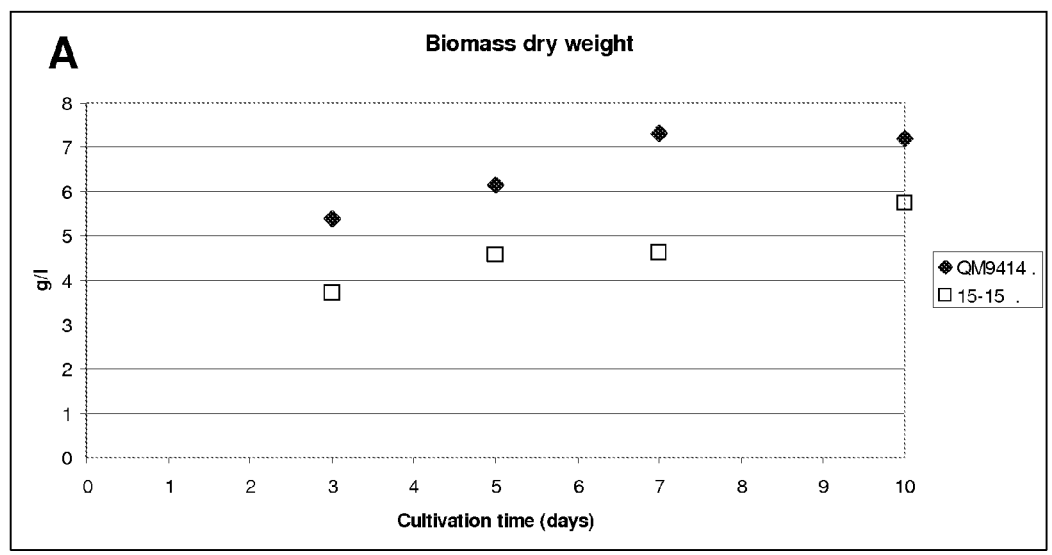
FIG. 1-5 present the results of protein production by strains genetically modified to overexpress a specific gene.
Figure 1:
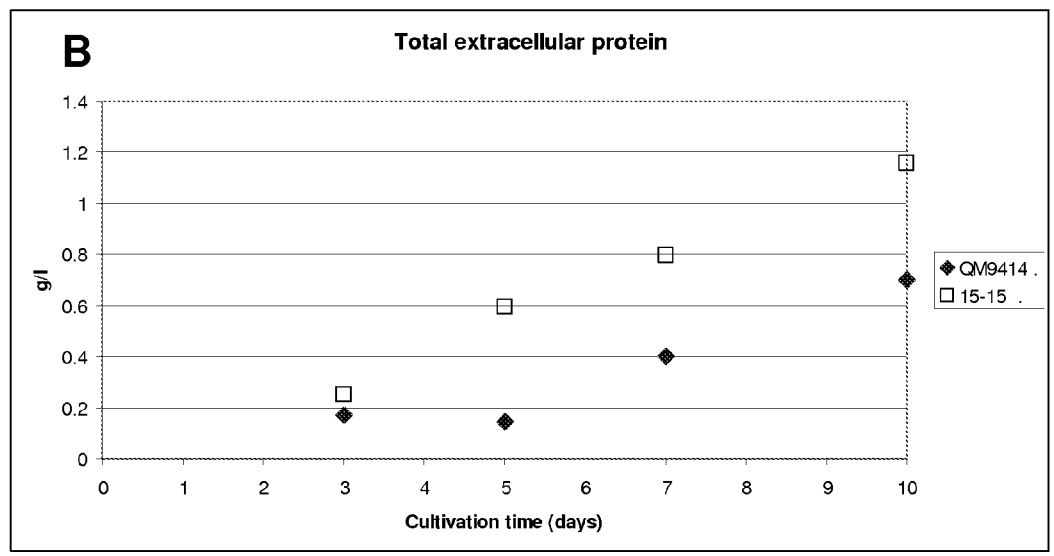
Figure 1:
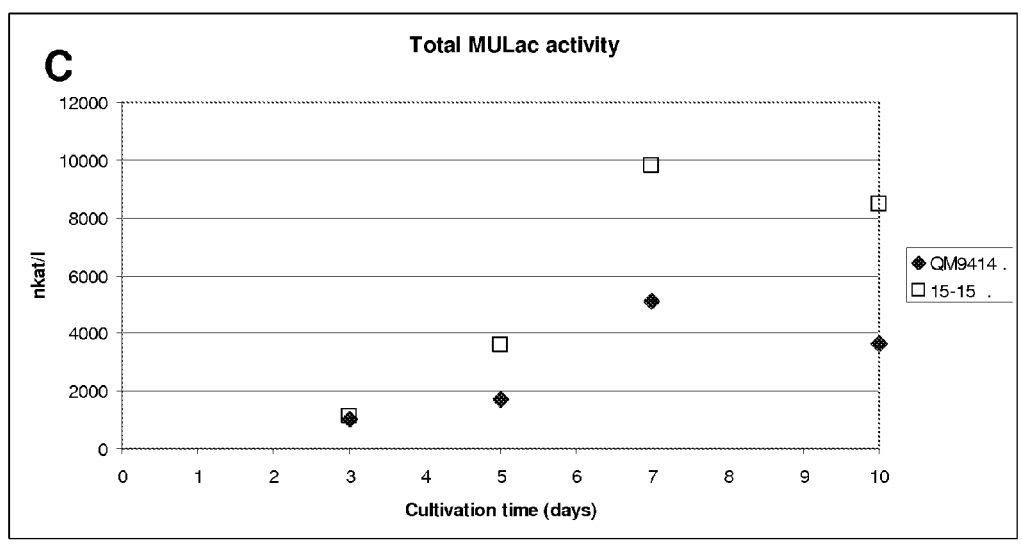
Figure 1:
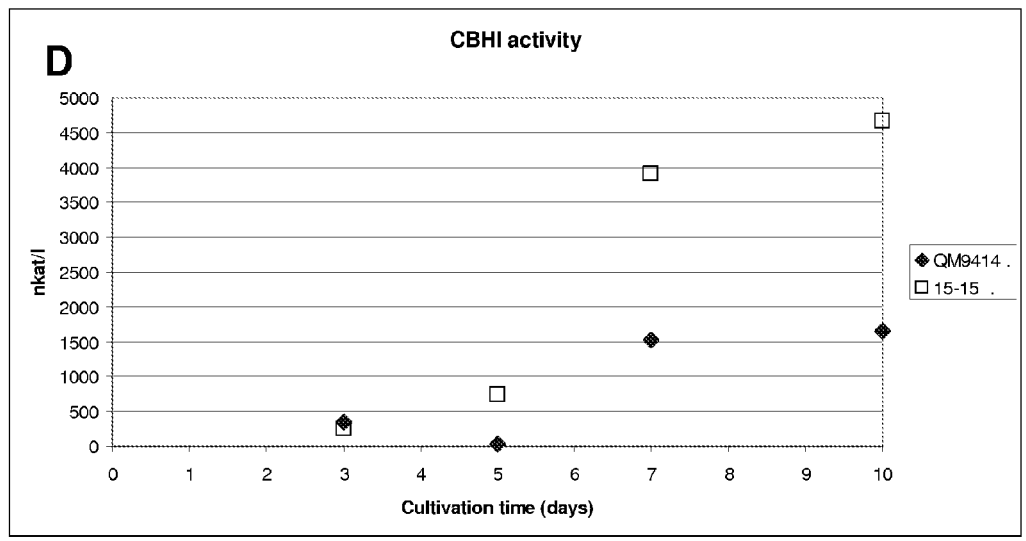
Figure 1:
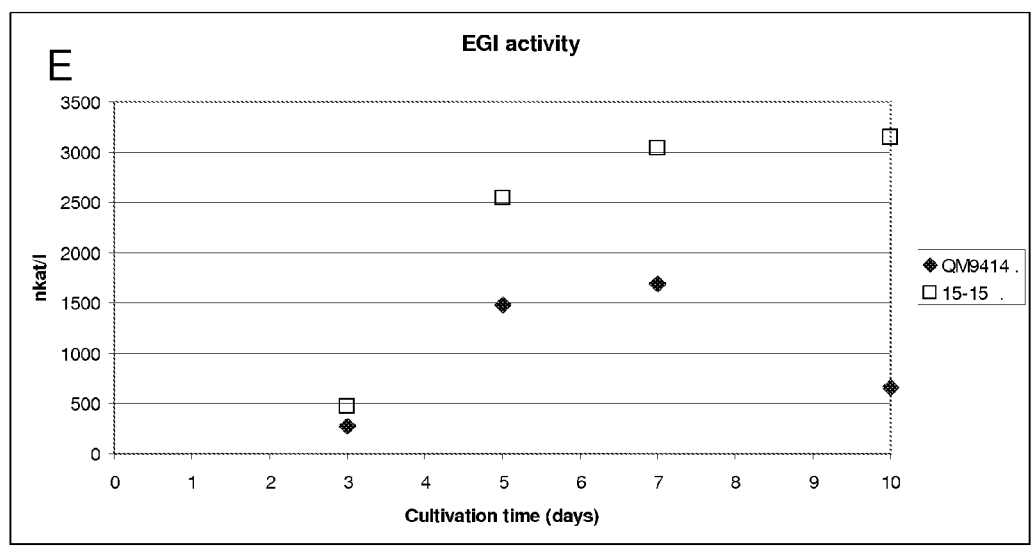
Figure 1:
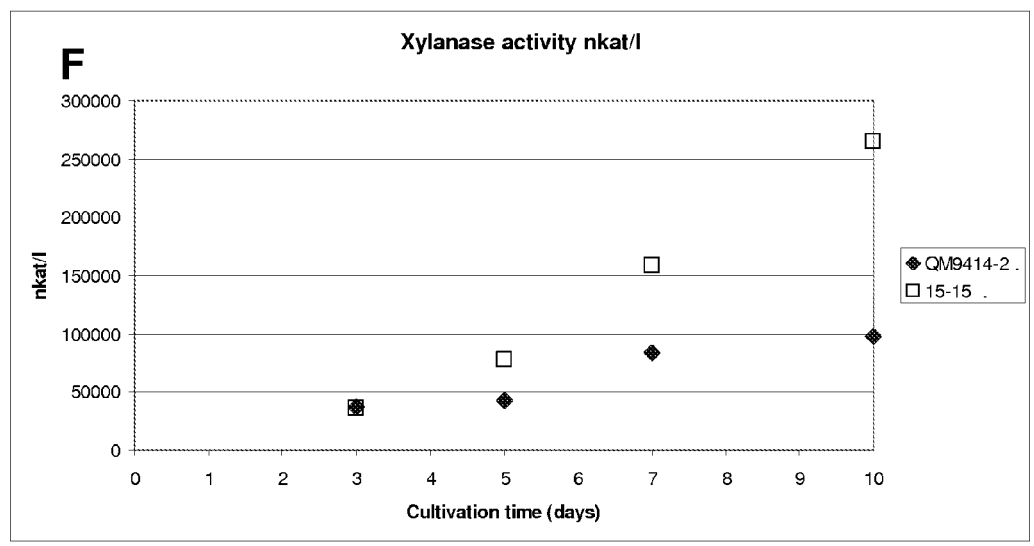
Figure 1:
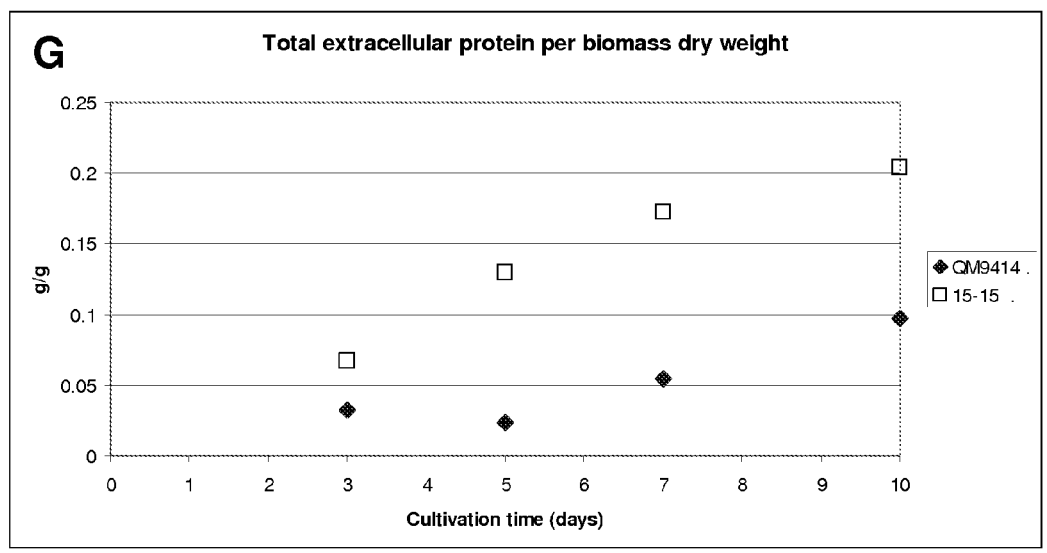
Figure 1:
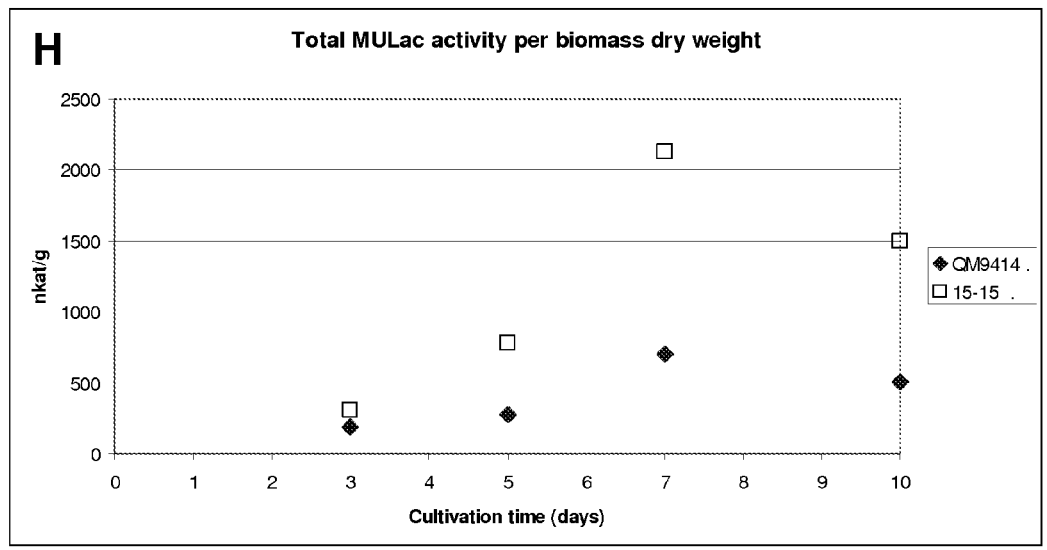
Figure 1:
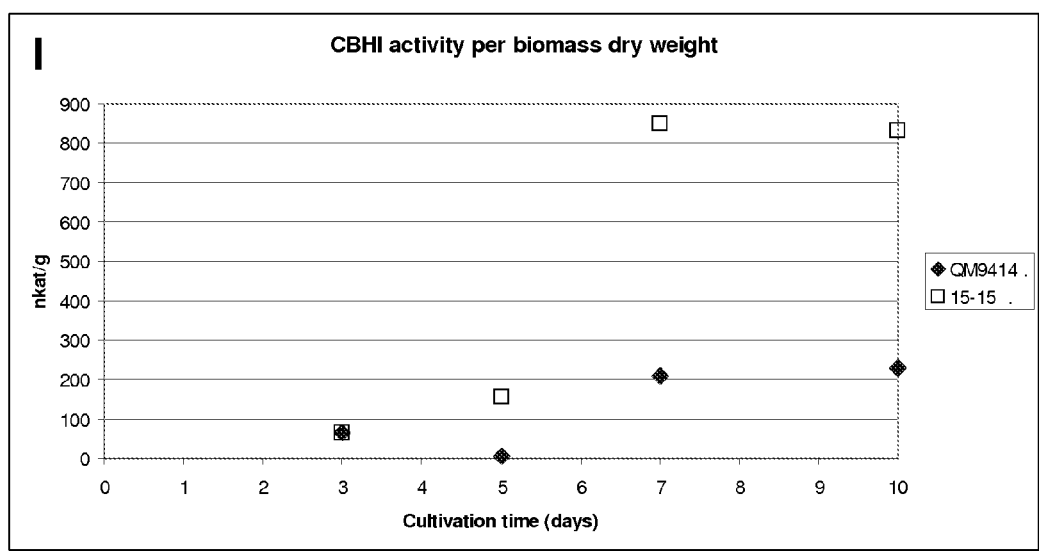
Figure 1:
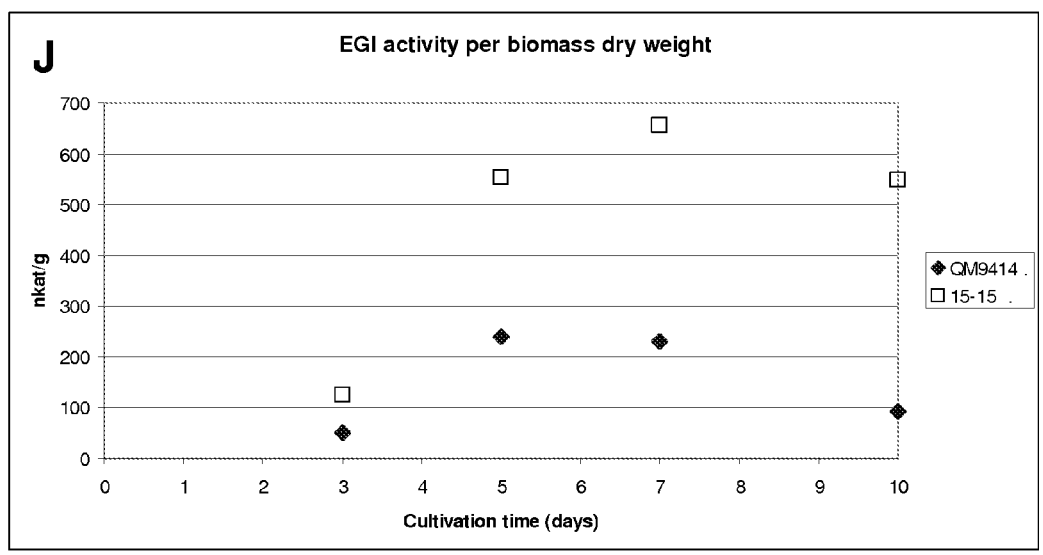
Figure 1:
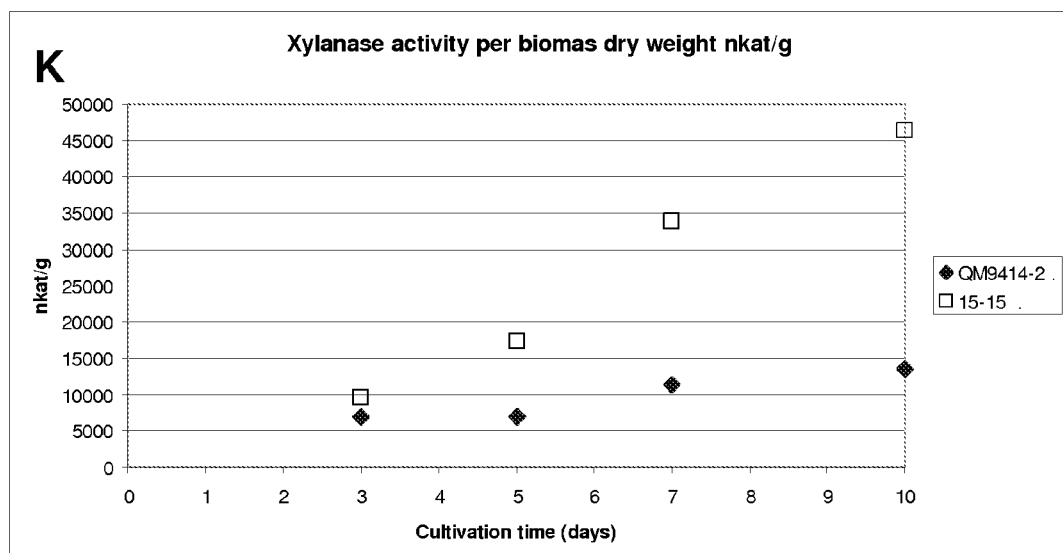

The present invention relates to improved production of various proteins in filamentous fungi. The invention is based on the finding of regulatory factors which affect the production of various proteins, in particular hydrolytic enzymes. Within the scope of the present invention are cellulases, such as cellobiohydrolases, endoglucanases and β-glucosidases; and hemicellulases, such as xylanases, mannases, β-xylosidases; and side chain cleaving enzymes, such as arabinosidases, glucuronidases, acetyl xylan esterases; and other lignocellulose degrading enzymes, in particular pectinases, such as endo- and exopolygalacturonases, pectin esterases, pectin and pectin acid lyase; and ligninases, such as lignin peroxidases, Mn peroxidases, laccases; amylolytic enzymes, such as α-amylases, glucoamylases, pullulanases, cyclodextrinases; hydrophobins; proteases (serine, aspartic, glutamic, metallo proteases, acidic, alkaline)); invertases; phytases; phosphatases, and hydrophobins.

By overexpressing specific genes and/or by making deficient specific genes which encode the regulatory factors in the fungal host, it is possible to increase or alter the production of endogenous proteins, in particular hydrolytic enzymes, such as cellulases, hemicellulases, lignocellulose degrading enzymes, other proteins involved in the degradation of lignocellulosic material or other proteins, typically secreted proteins. It is also possible to produce heterologous or recombinant proteins under the regulation of the promoters of the affected genes, such as cellulase or hemicellulase gene promoters, or promoters of other genes encoding proteins involved in the degradation of lignocellulosic material or other secreted proteins, by good yield in the modified host.

Described herein are methods used in modifying filamentous fungi hosts, such as *Trichoderma, Aspergillus, Fusarium, Neurospora, Talaromyces, Phanerochaete, Chrysosporium* and *Penicillium*. In these methods are used genes selected based on expression of the genes in cultures grown on different substrates and by sequence data of the genes. The sequence preferably comprises a sequence domain characteristic for genes encoding regulatory proteins, such as transcription factors, other transcriptional regulators, protein kinases, proteins involved in histone modification or chromatin remodelling, or the genes are preferably co-regulated with cellulase or hemicellulase genes in the genome of a filamentous fungus host.

"Overexpression of a gene" (here in particular a regulating gene) can be carried out for example by introducing into a fungus host an additional copy or copies of a specific gene, or expressing the gene under another promoter resulting in increased expression of the gene, or otherwise genetically modifying the fungus host so that either the gene is more abundantly expressed or that the activity of the gene product is increased. The effect of overexpression of a gene on protein production can be studied by culturing the modified host under conditions suitable for protein production. The effect on the production of an endogenous protein or proteins can be studied by determining for example a specific enzyme activity, determining the amount of total protein, or determining the amount of specific endogenous or heterologous protein produced.

"Making deficient of a gene" means either a genetic modification of the fungus host to delete or truncate a specific gene (here in particular a regulating gene) or a genetic modification of the fungus host resulting in reduced or lacking expression of the gene or reduced or lacking activity of the gene product by any suitable method. By "inactivation" is meant a genetic modification (usually deletion) resulting in complete loss of activity of a gene product. In this invention, the effect of the genetic modification of a specific gene on protein production can be studied by determining for example a specific enzyme activity, determining the amount of total protein, or determining the amount of specific endogenous or heterologous protein produced.

By "a regulatory gene" is meant here a gene whose function has an effect on production of proteins by the fungal host. "Overexpression of the gene" (as described above) or "making deficient of a gene" (as described above) has an effect on protein production by the fungus. The gene can encode for example a transcription factor, other transcriptional regulator, a protein kinase, a protein involved in histone modification or chromatin remodelling, or other regulatory protein.

By "inducing substrates" are meant here substrates capable of inducing the production of hydrolytic enzymes or lignocelluloses degrading enzymes, such as cellulase or hemicellulase, other protein involved in the degradation of lignocellulosic material, or other proteins, typically secreted proteins, or proteins produced using promoters of genes encoding secreted proteins. For the purpose of studying the genes encoding the mentioned enzymes, for example substrates, such as Avicel®, pretreated wheat straw, pretreated spruce, lactose, spent grain extract or sophorose, or other plant derived carbon sources, can be used. Pretreatment of spruce and wheat can be carried out by using steam explosion and washing the treated material. The fibrous fraction of the material can be used for the induction.

In one aspect improved production may mean improved production of a desired enzyme or other protein. As disclosed herein a filamentous fungus host may be constructed to overexpress a specific regulatory gene or genes, or may be constructed to be deficient in a specific other regulatory gene or genes, in order to improve the protein production.

By "suitable culture conditions for protein production" is meant here any culture conditions suitable for producing a desired protein or a combination of desired proteins. Conditions for producing hydrolytic enzymes or lignocelluloses degrading enzymes, such as cellulase or hemicellulase, other protein involved in the degradation of lignocellulosic material or for many secreted or other proteins, are well known for a person skilled in the art.

By "improved production" is here meant in one aspect increased amount of protein produced. The protein may be produced into the culture medium or into the host cell, preferably into the culture medium. Increased production may be detected for example as higher maximal level of protein or enzymatic activity, such as cellulase or hemicellulase activity, or total extracellular protein produced as compared to the parent host. In addition, or alternatively, improved protein production may be detected as a higher level of produced enzymatic activity or protein produced at any time point of cultivation which results in higher production level at earlier stages in cultivation and thus in faster production process as compared to parent host strain. Improved production may mean also increased production of secreted protein or enzymatic activity per biomass amount in the culture. Protein production by a lower amount of biomass is beneficial due to easier down stream-processing of the protein product and reduced consumption of nutrients during the production process. Also, a desired effect of the genetic manipulation of the production strain is lowered viscosity of the production culture due to e.g. lowered biomass amount in the production process or due to other properties of the strain. Cellulase and hemicellulase activities can be measured using a variety of methods using different substrates (for examples of the methods, see: Zhang Y. H., Hong J., Ye X., Cellulase assays, Methods Mol. Biol., (2009), 581:213-231; Sharrock K. R., Cellulase assay methods: a review, J. Biochem. Biophys. Methods. (1988), 17:81-105; T. K. Ghose, Measurement of cellulase activities, (1987), Pure & Appl. Chem., 59, 257-268; T. K. Ghose and V. S. Bisaria, Measurement of hemicellulase activities. Pure & Appl. Chem., (1987), 59, 1739-1752). Cellulase activity can be measured e.g. as enzymatic activity against the substrate, 4-methylumbelliferyl-β-D-lactoside (MULac). Methods for measuring the combined activity of CBHI, EGI and β-glucosidase (referred here as "total MULac" activity), as well as the separate activities of the enzymes, using MULac as substrate have been described (Bailey and Tahtiharju, 2003; Collen et al., 2005; van Tilbeurgh et al., 1982, 1985, 1988). Other substrates often used for cellulase activity measurements include e.g. CMC cellulose, hydroxyethylcellulose and filter paper. The hemicellulase activity can be measured e.g. as activity against the birch xylan substrate (Bailey et al., 1992, Bailey M. J., Biely, P. and Poutanen, K. (1992) Interlaboratory testing of methods for assay of xylanase activity. J. Biotechnol. 23: 257-270), and production of total extracellular protein by using any of the methods for measurement of protein concentration known in the art, for example using Bio-Rad Protein Assay (Bio-Rad). Growth and progress of the cultivation of filamentous fungi can be determined by measuring the production of biomass and by measuring the pH of the culture medium. Induction of protein production, and differences in gene expression level can be analysed by isolation of RNA and subjecting the samples to micro array hybridisation analysis or Northern hybridisation or TRAC analysis (Rautio, J. J., Smit, B. A., Wiebe, M., Penttilá, M. & Saloheimo, M. 2006. Transcriptional monitoring of steady state and effects of anaerobic phases in chemostat cultures of the filamentous fungus

*Trichoderma reesei*. BMC Genomics 7, article number 247. 15 p. 10.1186/1471-2164-7-247)

Improved CBHI activity may be detected by higher production level of enzyme activity against MULac substrate using a method modified for analysis of CBHI activity.

Improved EGI activity may be detected by higher production level of enzyme activity against MULac substrate and especially by higher activity against MULac substrate under conditions measuring specifically the activity of EGI.

The increased hemicellulase production may be detected by higher production level of enzyme activity against birch xylan substrate.

In one embodiment the protein can be an endogenous protein, in particular a hydrolytic enzyme, such as cellulase, hemicellulase or lignocellulose degrading enzyme, or other secreted protein. More specifically the protein can be a cellulase or hemicellulase.

In another embodiment the protein may be any protein which is produced under the promoter of the affected endogenous genes. The protein may be produced for example under various cellulase or hemicellulase gene promoters, such as promoters of genes encoding CBHI, EGI or XYNI.

Improved protein production may mean altered content of the proteins produced by the fungus host, and production of a desired protein or a protein mixture. As disclosed herein a filamentous fungus host may be constructed to overexpress a specific regulatory gene or genes, or may be constructed to be deficient in a specific other regulatory gene or genes, in order to alter the protein production compared to the parental host.

By the term "endogenous proteins" are meant here proteins which are natural products of a filamentous fungus host.

By "a heterologous protein" is meant a protein that is not a natural product of the fungal species.

By "recombinant proteins" are meant here proteins that are not natural products of a filamentous fungus or that are produced by a non-natural construction in a filamentous fungus. DNA sequences encoding desired homologous or heterologous proteins may be transferred by a suitable method to a host.

By "secretable protein" or "secreted protein" is meant here a protein that is secretable or secreted outside of the host cell to the culture medium.

By increased protein production is meant protein production which is a least 3%, preferably at least 5%, more preferably at least 10%, still more preferably at least 20%, still more preferably at least 30% or most preferably at least 50% better than protein production by using the parent fungal host strain which has not been genetically modified.

By reduced protein production is meant protein production which is at least 3%, preferably at least 5%, more preferably at least 10%, still more preferably at least 20%, still more preferably at least 30% or most preferably at least 50% lower than protein production by using the parent fungal host strain which has not been genetically modified.

One embodiment of the invention comprises the expression of gene sequences responsible of regulating the production of hydrolytic enzymes. The genes may increase or decrease the enzyme production, or they may increase the production of some enzyme activities and decrease other enzyme activities.

"Genetical modification" of a filamentous fungus host means here any genetic modification method by which a filamentous fungus host is modified to overexpress a specific regulatory gene or to gain modified properties of the gene or genes and/or to be deficient of the gene or genes, Genetical modification methods for the strains of *Trichoderma, Aspergillus, Fusarium, Neurospora, Phanerochaete, Talaromyces, Chrysosporium* and *Penicillium*. are available and well known for a person skilled in the art (Sambrook et al., 1989, Penttilä et al., 1987; Jain et al., 1992; Austin et al., 1990; Bull et al., 1988; Maier et al., 2005; Akileswaran et al., 1993).

Penttilä M, Nevalainen H, Rättö M, Salminen E, Knowles J. (1987) A versatile transformation system for the cellulolytic filamentous fungus *Trichoderma reesei*. Gene. 1987; 61:155-64.

Jain S, Durand H, Tiraby G. (1992) Development of a transformation system for the thermophilic fungus *Talaromyces* sp. CL240 based on the use of phleomycin resistance as a dominant selectable marker. Mol Gen Genet. 1992 September; 234(3):489-93.

Austin B, Hall R M, Tyler B M. (1990) Optimized vectors and selection for transformation of *Neurospora crassa* and *Aspergillus nidulans* to bleomycin and phleomycin resistance. Gene. 1990 93:157-62.

Bull J H, Smith D J, Turner G. (1988) Transformation of *Penicillium chrysogenum* with a dominant selectable marker. Curr Genet. 1988 May; 13(5):377-82.

Maier F J, Malz S, Lösch A P, Lacour T, Schafer W. (2005) Development of a highly efficient gene targeting system for *Fusarium graminearum* using the disruption of a polyketide synthase gene as a visible marker. FEMS Yeast Res. 2005 April; 5(6-7):653-62.

Akileswaran L, Alic M, Clark E K, Hornick J L, Gold M H. (1993) Isolation and transformation of uracil auxotrophs of the lignin-degrading basidiomycete *Phanerochaete chrysosporium*. Curr Genet. 1993; 23(4):351-6.

By "gene" is meant here in particular a gene or genes encoding regulatory proteins, such as transcription factors, other transcriptional regulators, protein kinases, proteins involved in histone modification or chromatin remodelling, or genes located near cellulase or hemicellulase genes (co-expressed) in the genome of a filamentous fungus host. The genes have been selected by using the method as described herein. The function of the genes has been exemplified in *Trichoderma*, in particular in *T. reesei* which show the effect of these genes in protein production. Modification of the genes in other filamentous fungi, in particular *Aspergillus* will be useful for improved protein production. The "gene" in the present invention is preferably a *Trichoderma* gene. Within the scope of the present invention are also the closest homologues of the genes in other species of filamentous fungi and nucleotide sequences hybridizing under stringent conditions to said genes or said homologues. Within the scope of the present invention are also fragments, derivatives or other nucleotide sequences of said genes hybridizing under stringent conditions to said genes or said homologue. The "gene" may be isolated, which means that it is isolated from its natural components. The "gene" may be partly or completely synthetic. Within the scope of the present invention are also derivatives of said gene, which refers to nucleic acid sequences comprising deletions, substitutions, insertions or other modifications compared to said gene, but having the same or equivalent function as said gene.

A "fungal host" denotes here any fungal host strains selected or genetically modified to produce (or not produce) efficiently a desired product and is useful for protein production for e.g. analytical, medical or industrial use. A fungal host is in particular "a fungal production host" that is suitable for industrial production of certain protein products. The host strain is preferably a recombinant strain modified by gene technological means to efficiently produce a product of interest. The fungal host may belong for example to *Trichoderma, Aspergillus, Fusarium, Neurospora, Talaromyces, Phanerochaete, Chrysosporium* or *Penicillium* genera. Typically the host is *Trichoderma* or *Aspergillus* host.

The "closest homologue of a *Trichoderma* gene" in other species of filamentous fungi means here a gene that has the highest percentage of identical nucleotides with the *Trichoderma* gene of all the genes of the organism; or a gene whose protein product has the highest percentage of identical amino acids with the protein product encoded by the *Trichoderma* gene of all the gene products of the organism. The sequence identity of homologous regulatory genes in different organisms is typically very low. Typically, the sites binding either to DNA or other protein factors involved in the regulation event share homology, but the intervening sequences between these sites may not be conserved. Therefore the total % of sequence identity of homologous regulatory genes in different organisms remains relatively low. However, the percentage of sequence identity in the aligned nucleotide sequence can be used as a measure to identify the closest homologue of the gene in the other organism, thus a likely functional counterpart of the gene in the other organism. Software and algorithms for homology searches as well as public databases with whole geneome sequence information for a variety of species exist, such as the BLAST program (Stephen F. Altschul, Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402. Reference for compositional score matrix adjustment: Stephen F. Altschul, John C. Wootton, E. Michael Gertz, Richa Agarwala, Aleksandr Morgulis, Alejandro A. Schaffer, and Yi-Kuo Yu (2005) "Protein database searches using compositionally adjusted substitution matrices", FEBS J. 272:5101-5109) and the NCBI database.

A specific "gene" is here represented by a specific sequence (SEQ ID NO)". The effect of the gene has been shown by using the sequence of a specific SEQ ID NO (which is here a *Trichoderma* sequence). The sequence may comprise additional sequence in front of and/or after the coding region of the gene. As described here, instead of the *Trichoderma* sequence, the closest homologue from another filamentous fungus could be used. As is known to a person skilled in the art, also sequences hybridizing under stringent conditions to the *Trichoderma* sequence or to its closest homologue, could be used." wherein stringent conditions refer here to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65 degree C.

The detection methods of cellulase activity, CBHI activity or EGI activity are well known for a person skilled in the art. The methods are described for example in Bailey and Tahtiharju, 2003; Collen et al., 2005; van Tilbeurgh et al., 1982, 1985, 1988. Collén, A., Saloheimo, M., Bailey, M., Penttilä, M. & Pakula, T. M. (2005) Protein production and induction of the unfolded protein response in *Trichoderma reesei* strain Rut-C30 and its transformant expressing endoglucanase I with a hydrophobic tag. *Biotech. Bioeng.* 89, 335-344. Bailey M J, Tahtiharju J. 2003. Efficient cellulase production by *Trichoderma reesei* in continuous cultivation on lactose medium with a computer-controlled feeding strategy. Appl Microbiol Biotechnol 62:156-62. van Tilbeurgh H, Claeyssens M, de Bruyne C. 1982. The use of 4-methylumbelliferyl and other chromophoric glycosidases in the study of cellulolytic enzymes. FEBS Lett 149:152-156. van Tilbeurgh H, Loontiens F G, de Bruyne C K, Claeyssens M. 1988. Fluorogenic and chromogenic glycosides as substrates and ligands of carbohydrates. Methods Enzymol 160:45-59. van Tilbeurgh H, Pettersson G, Bhikabhai R, De Boeck H, Claeyssens M. 1985. Studies of the cellulolytic system of *Trichoderma reesei* QM 9414. Reaction specificity and thermodynamics of interactions of small substrates and ligands with the 1,4-beta-glucan cellobiohydrolase II. Eur J Biochem 148:329-34.

The cultures of the strains modified for the regulatory genes can be analysed for the produced protein pattern more in detail using a broader set of enzyme activity measurements specific for different enzymes. In addition, the produced protein pattern can be analysed using 2D gel electrophoresis followed by identification of the proteins by mass spectrometry. The 2D gel analysis can reveal also quantitative differences in the produced protein patterns between the cultures of the different strains. This information can reveal specific sets of produced proteins that are affected by the specific genetic modification. Furthermore, additional genetically modified strains can be constructed to be able to analyse the effects of both the overexpression and the deficiency (typically deletion) of the gene, and by these means to reveal the target genes and proteins whose function is affected by the modification of the gene, and to demonstrate the effect of the specific gene modification on the produced protein pattern. These genetically modified strains can also be subjected to transcriptional profiling in order to elucidate the effect of the genetic modification on the gene expression levels and to reveal target genes affected by the modification. The information of the effects of the genetic modification on the produced protein pattern (from the enzyme assays and 2D gel analysis of the culture supernatants) as well as information on the transcriptional responses caused by the genetic modification, and the target genes for the regulatory events it is possible to modify the protein production properties and efficiency, as well as the composition of the protein mixture produced into the culture medium in a defined way.

The improvement in protein production process can mean either increased production of all the secreted proteins, or improved production of a specific set of proteins, or reduced production of unwanted products, or a faster or shorter production process for the protein, or a production process with less consumption of nutrients for other products than proteins (e.g. for biomass or unwanted side-products), or better physico-chemical properties protein producing unit (e.g. less viscose cultivation, better morphology of the production host), or better downstream processing properties of cultivation and the protein product, or better physico-chemical quality of the product.

According to specific embodiments of the invention one or more of the gene sequences tre77513 (SEQ ID NO:1), tre80291 (SEQ ID NO:2), tre41573 (SEQ ID NO:3), tre74765 (SEQ ID NO:4), tre64608 (SEQ ID NO:5) (Table 1); or the closest homologue of at least one of said sequences in *Trichoderma, Aspergillus, Fusarium, Neurospora, Talaromyces, Phanerochaete, Chrysosporium* or *Penicillium*; or a fragment or derivative of any of said genes or other sequence hybridizing under stringent conditions to at least one of said sequences or said homologues, are overexpressed in a fungus host. The overexpression of these genes in the genetically modified host causes increased production of cellulase, hemicellulase, other proteins involved in degradation of lignocellulosic material and/or other proteins, typically secreted proteins and/or of total extracellular protein as compared to the parental host, or proteins produced using promoters of genes encoding secreted proteins. This can be detected either as higher maximal level of enzymatic activity or protein produced during the cultivation or as a higher level of produced enzymatic activity or protein produced at any time point of cultivation resulting in higher production level at earlier stages of cultivation and thus in faster production process as compared to parent host.

Cellulase activity can be measured e.g. as enzymatic activity against the substrate, 4-methylumbelliferyl-β-D-lactoside (MULac). Methods for measuring the combined activity of CBHI, EGI and β-glucosidase (referred here as "total MULac" activity), as well as the separate activities of the enzymes, using MULac as substrate have been described by Bailey and Tahtiharju, 2003; Collen et al., 2005; van Tilbeurgh et al., 1982, 1985, 1988. The hemicellulase activity can be measured e.g. as activity against the birch xylan substrate (Bailey et al., 1992, Bailey M. J., Biely, P. and Poutanen, K. (1992) Interlaboratory testing of methods for assay of xylanase activity. J. Biotechnol. 23: 257-270), and production of total extracellular protein by using any of the methods for measurement of protein concentration known in the art, for example using Bio-Rad Protein Assay (Bio.Rad).

It is advantageous, if one or more of genes tre77513 (SEQ ID NO:1), tre80291 (SEQ ID NO:2) or tre41573 (SEQ ID NO:3), still more preferably either one or both of genes tre77513 (SEQ ID NO:1) and/or tre80291 (SEQ ID NO:2) are overexpressed in a fungus host. The term "gene" encompasses here also the closest homologue of at least one of said sequences in *Aspergillus, Fusarium, Neurospora, Talaromyces, Phanerochaete, Chrysosporium* or *Penicillium*; or a fragment or derivative of said genes or other nucleotide sequence hybridizing under stringent conditions to at least one of said sequences or said homologues.

TABLE 1

| Plasmid | *T. reesei* gene | strain |
|---|---|---|
| pMH15 | tre77513 | 15-15 |
| pMH20 | tre80291 | 20-2 |
| pMH23 | tre41573 | 23-5 |
| pMH25 | tre74765 | 25-7 |
| pMH36 | tre64608 | 36-22 |

According to other specific embodiments of the invention the overexpression of one or more these genes causes increased production of extracellular protein in the culture medium.

Also other combinations of the mentioned genes can be overexpressed and/or made deficient in a fungus host to get a combined effect of the genes on protein production properties of the fungus host. Inactivation or reduced activity of one or more of mentioned genes may be beneficial to reduce production of unwanted side-products. Within the scope of protection are thus genetical modification of a fungus host by overexpression or by making deficient at least one of said genes. Overexpression of the above mentioned genes in filamentous fungus hosts was exemplified here by constructing *Trichoderma* strains expressing these genes. The expression of the same or corresponding genes i.e. closest homologues of said genes, in other filamentous fungi hosts, is within the scope of protection of the present invention.

The corresponding genes may also be either overexpressed or made deficient, as described above, also in other filamentous fungi hosts.

Also sequences hybridizing under stringent conditions to the *Trichoderma* genes or their closest homologues in other filamentous fungus hosts are within the scope of protection of the present invention. In the following text, by "gene" is meant also the closest homologue of the gene or sequences hybridizing into said gene or said homologue as herein described. By "gene" is in the following text meant also any fragment or derivative or modified form comprising deletions, substitutions, insertions or other genetic modifications, but having the same or equivalent function as the said "gene".

To exemplify the effect of the genes on protein production, the genes were overexpressed in *T. reesei* QM9414 host as described in the Examples 4-6.

The structure of the genes is similar in that they all comprise a sequence domain typical to genes encoding regulatory proteins, such as transcription factors as shown in Table 2.

TABLE 2

| Gene ID | | IPR001138, Fungal transcriptional regulatory protein, N-terminal | IPR007219, Fungal specific transcription factor | IPR011616, bZIP transcription factor, bZIP-1 | IPR008917, Eukaryotic transcription factor, Skn-1-like, DNA-binding | IPR001680, WD40 repeat | IPR001487, Bromodomain | IPR000210, BTB/POZ-like |
|---|---|---|---|---|---|---|---|---|
| tre77513 | pMH 15 | | x | | | | | |
| tre80291 | pMH 20 | x | | | | | | |
| tre41573 | pMH 23 | | | x | x | | | |
| tre74765 | pMH 25 | | | | | | x | x |
| tre64608 | pMH 36 | | | | | x | | |

The effect of gene tre77513 (FIG. 1), represented by SEQ ID NO:1, was exemplified by constructing strain *T. reesei* 15-15 overexpressing the gene. The overexpression of this gene caused increased production of total extracellular protein, hemicellulase activity (measured as xylanase activity), and cellulase activity (measured as total Mulac activity, CBHI or EGI activity). Biomass production in the cultivation was clearly decreased as compared to the cultures of parent host strain. The overexpression of gene tre77513 can be used in particular to increase cellulase or hemicellulase production, or the production of other secreted proteins. In addition, production of various heterologous proteins under the promoters of cellulase or hemicellulase genes (or similarly regulated promoters) can be produced at higher level by the strains overexpressing the gene as compared to the parent host strain. By overexpressing gene tre77513 it is possible to reduce biomass production during the production process as compared to the parent host strain. The advantage of reduced biomass production is easier down stream processing of the product and reduced carbon consumption for production of biomass. Therefore, more protein per carbon can be produced. In addition the product is likely to be less viscose.

Figure 2:
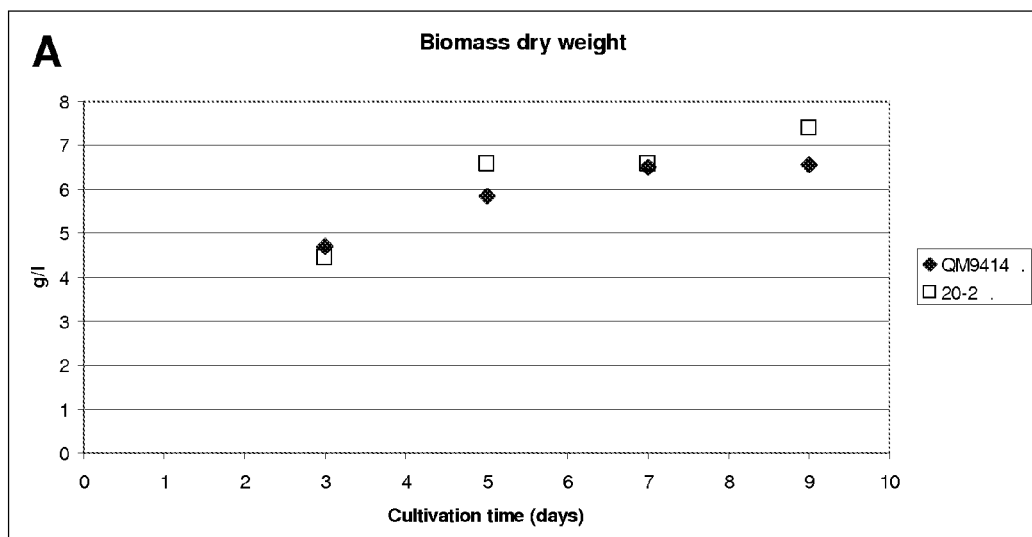
Figure 2:
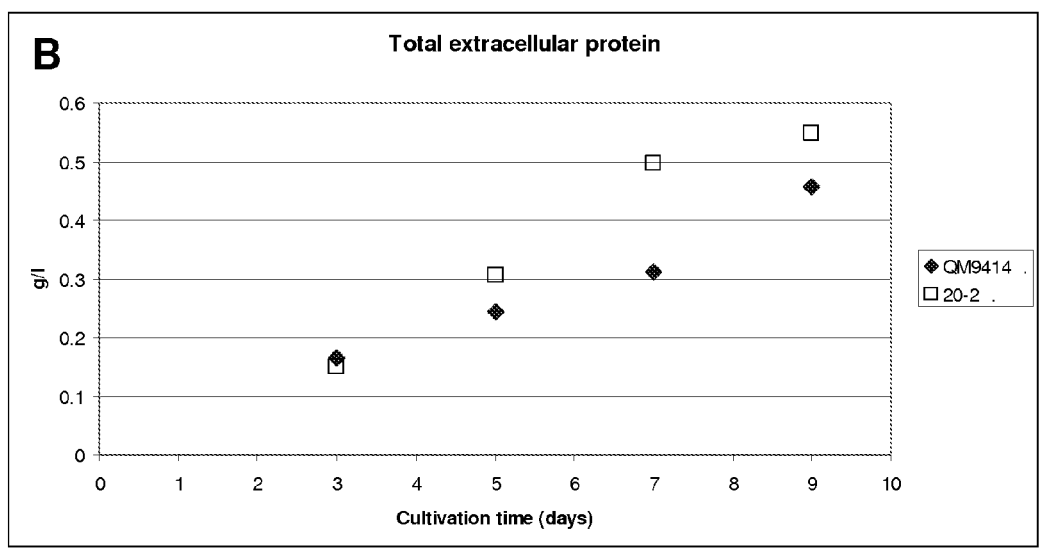
Figure 2:
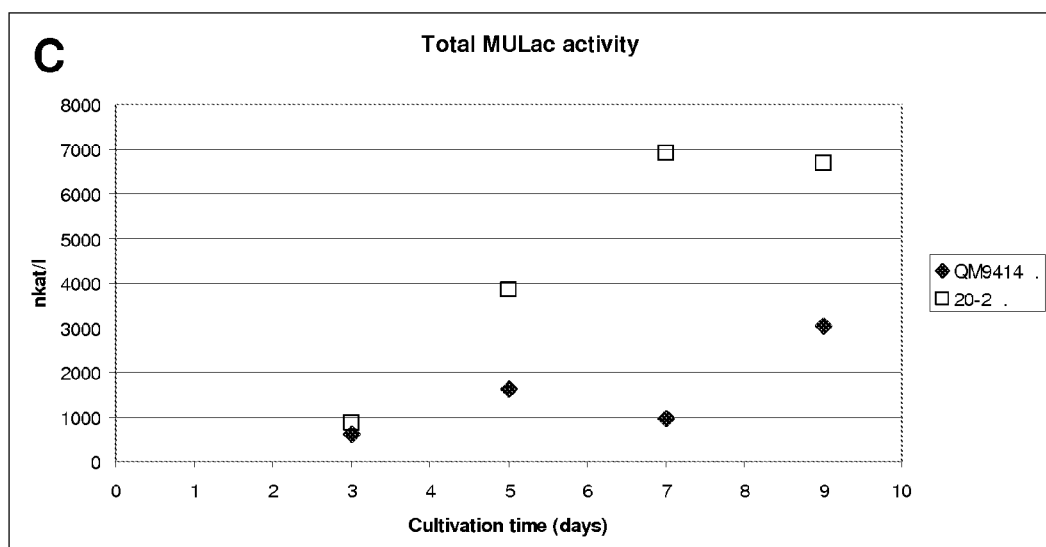
Figure 2:
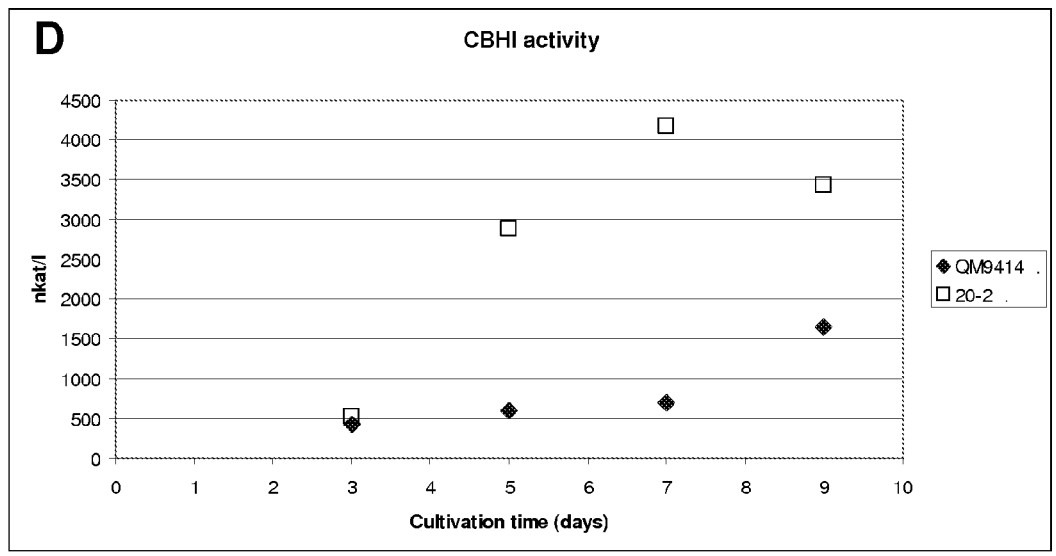
Figure 2:
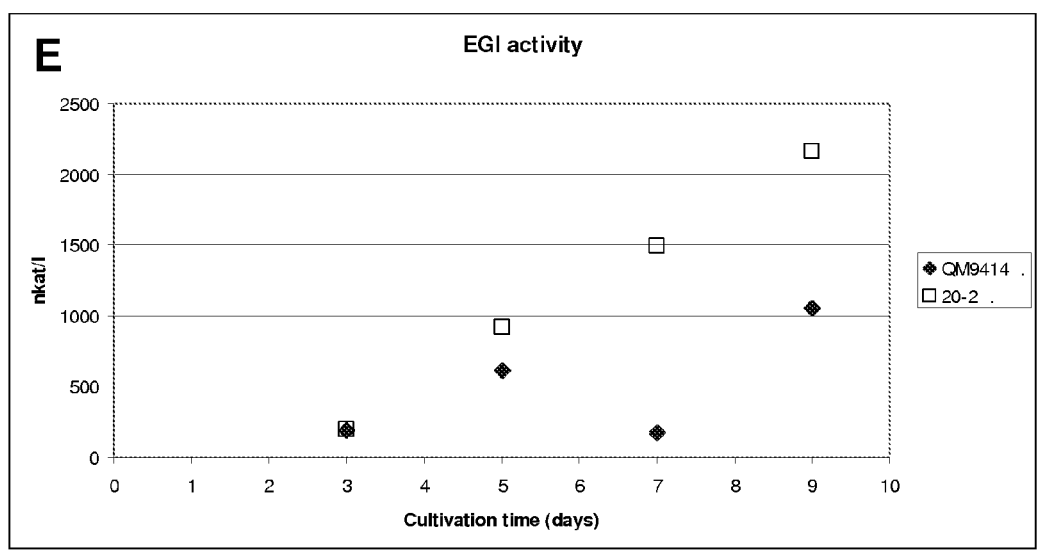
Figure 2:
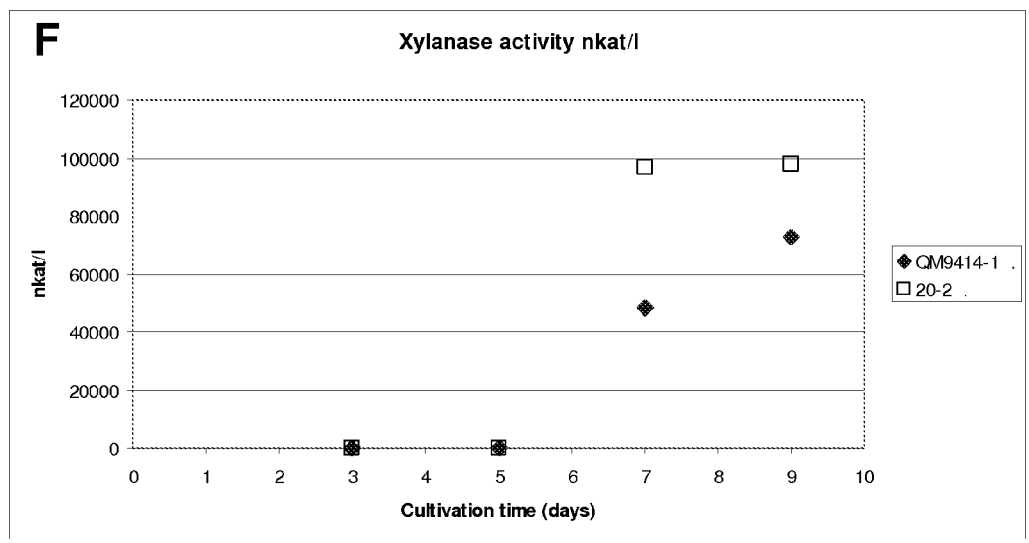
Figure 2:
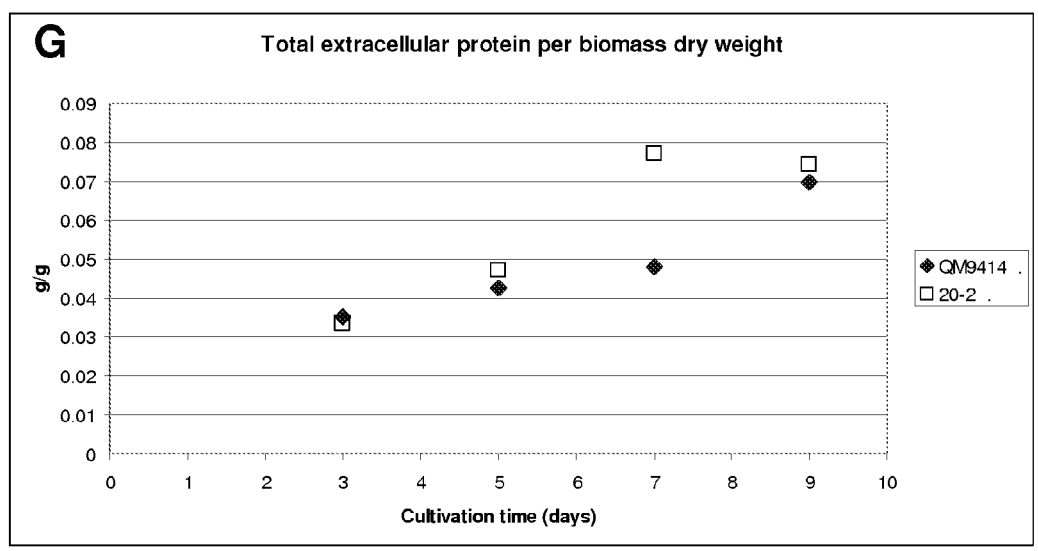
Figure 2:
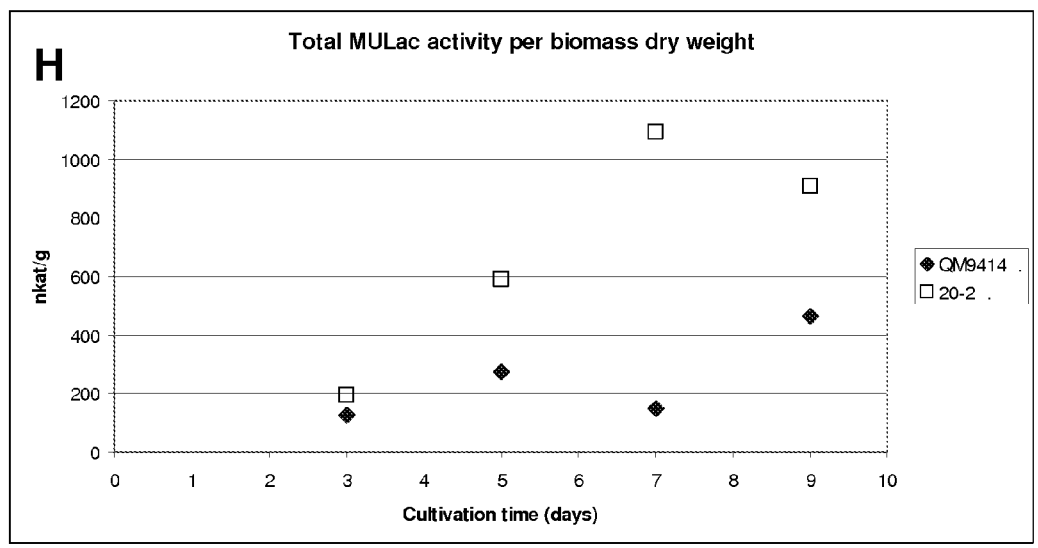
Figure 2:
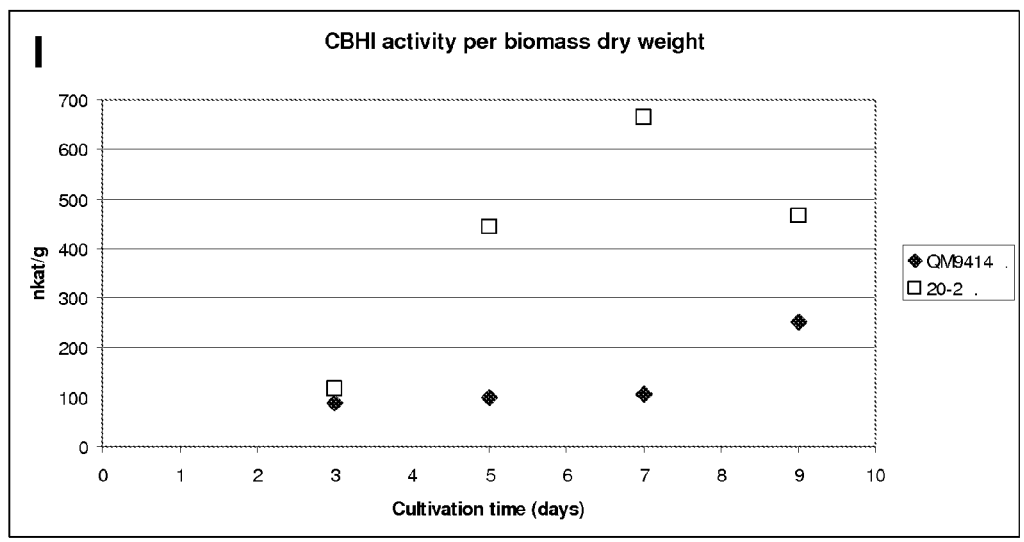
Figure 2:
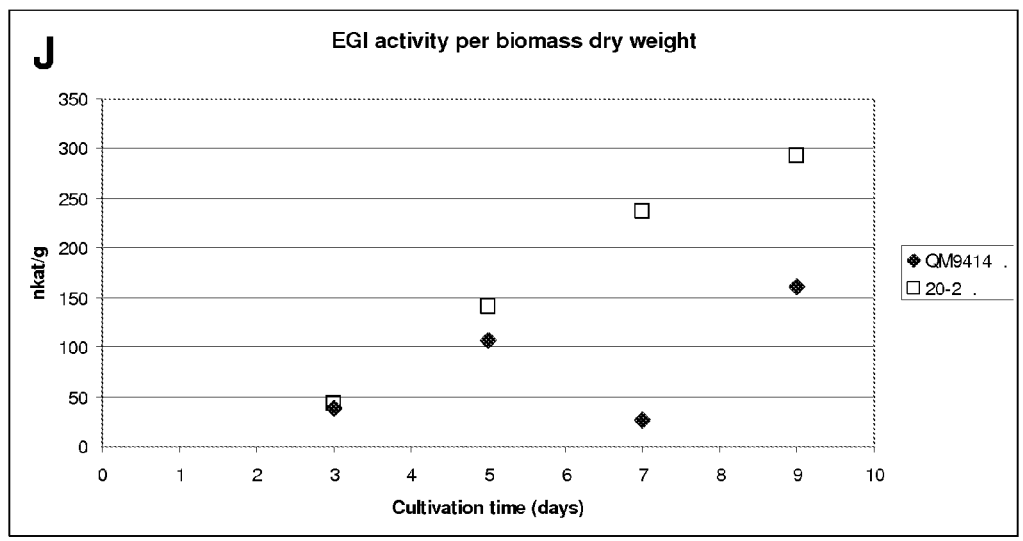
Figure 2:
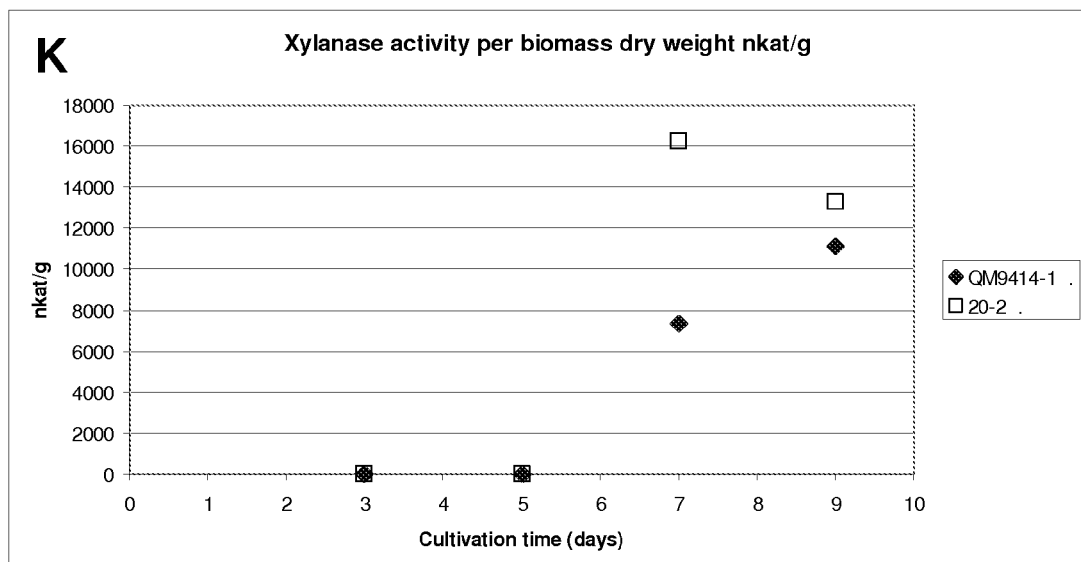

The effect of gene tre80291 (FIG. 2), represented by SEQ ID NO:2, was exemplified by constructing strain *T. reesei* 20-2 overexpressing the gene. The overexpression of this gene caused increased cellulase activity, measured as total Mulac, CBHI or EGI activity, increased hemicellulase activity, measured as xylanase activity, as well as increased production of total extracellular protein as compared to the parent host. The production process of the modified host was faster as compared to the parent host. The overexpression of gene tre80291 can be used in particular to increase cellulase or hemicellulase production, or the production of other secreted proteins. In addition, various heterologous proteins can be produced under the regulation of cellulase promoters. By overexpressing gene tre80291, it is possible to make the protein production process faster.

Figure 3:
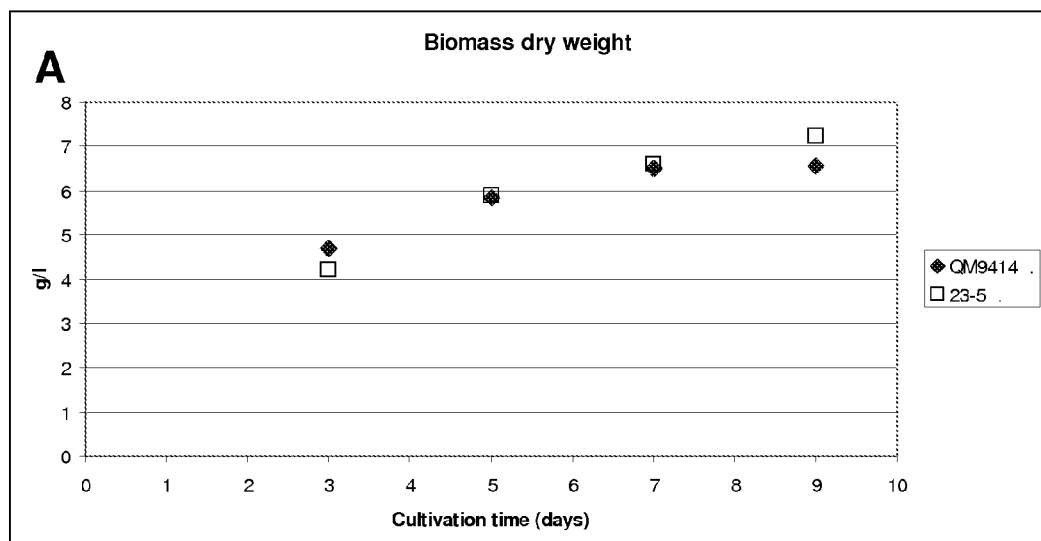
Figure 3:
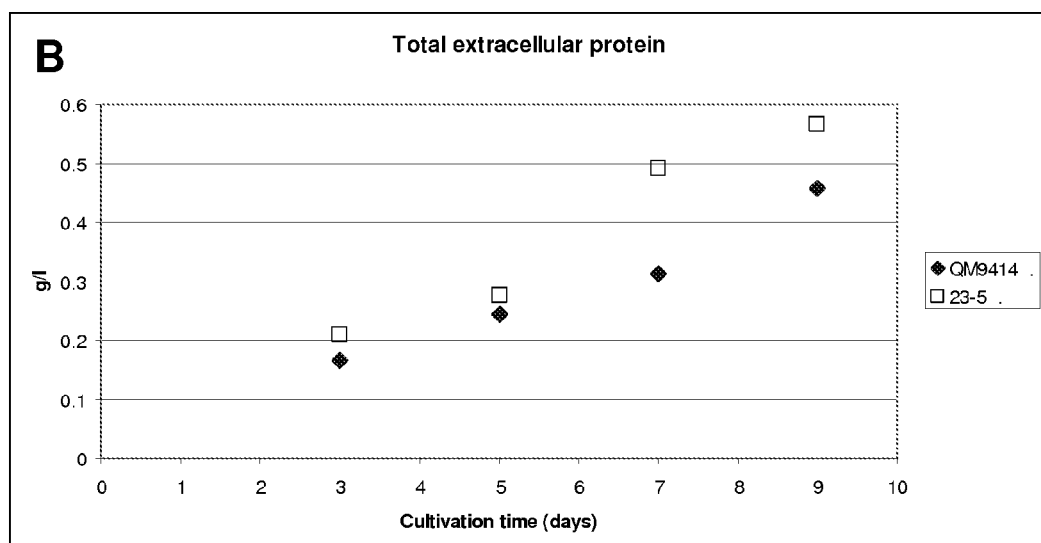
Figure 3:
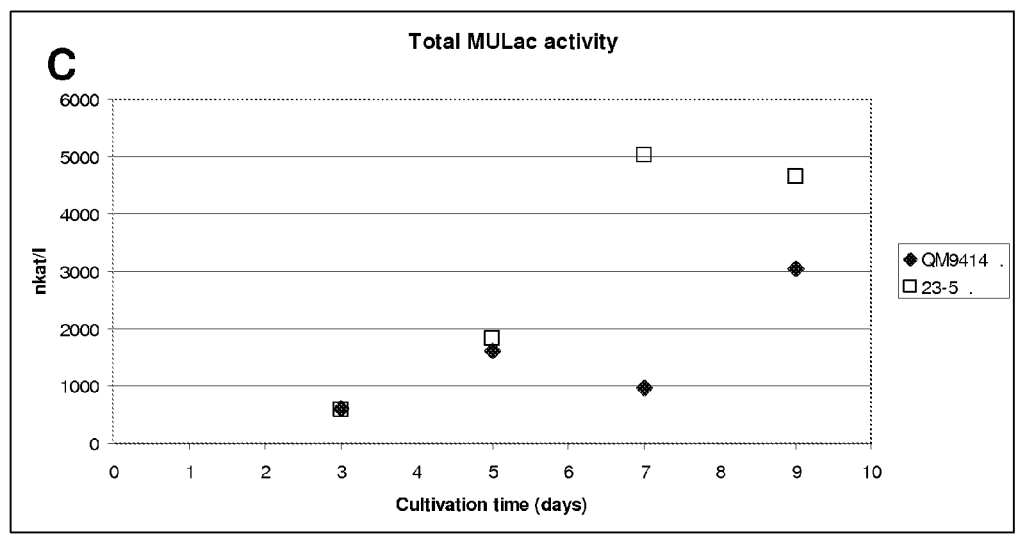
Figure 3:
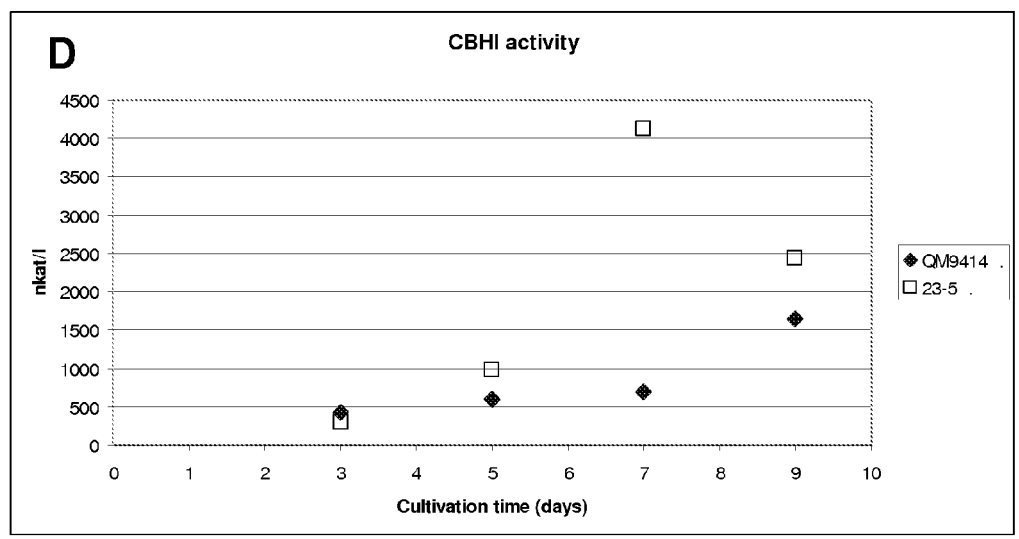
Figure 3:
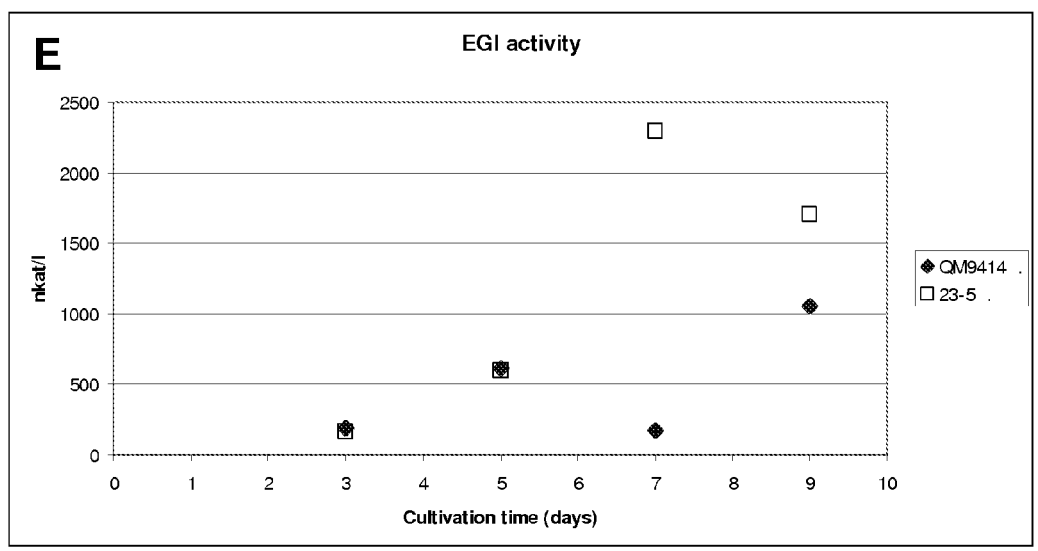
Figure 3:
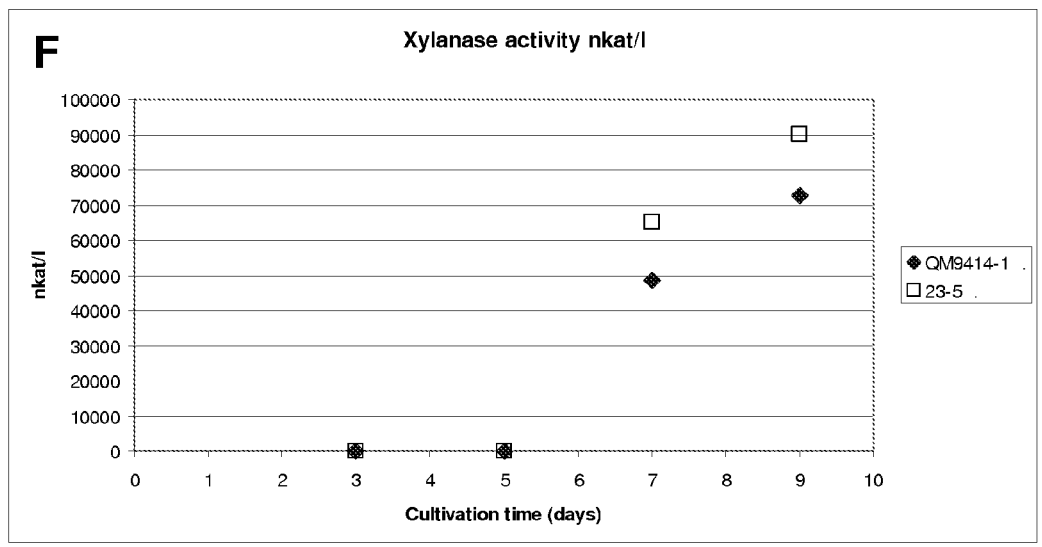
Figure 3:
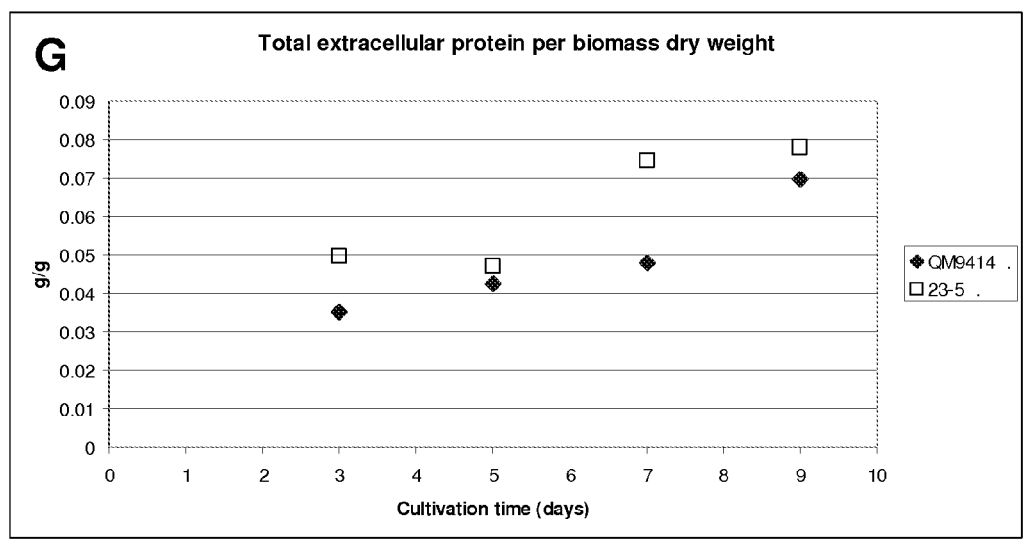
Figure 3:
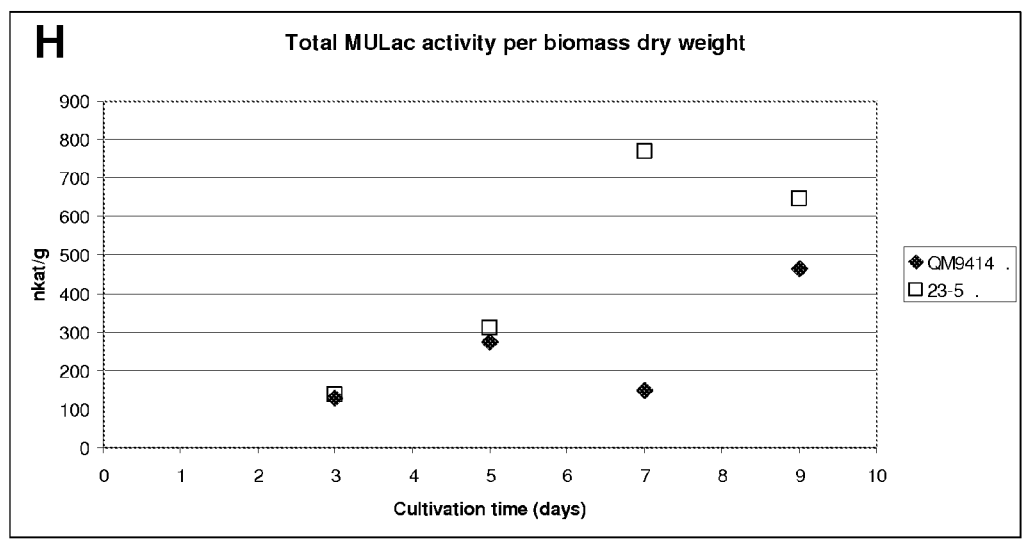
Figure 3:
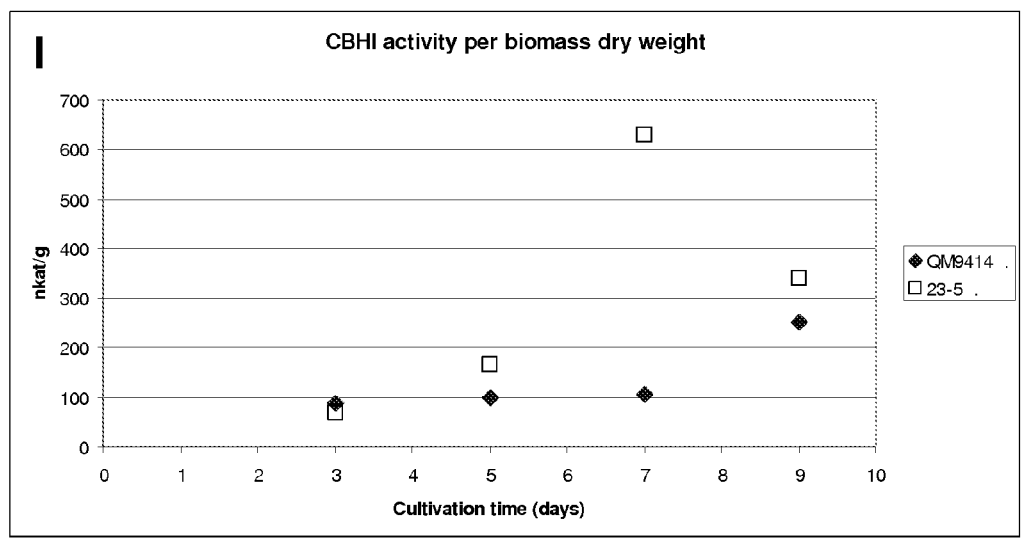
Figure 3:
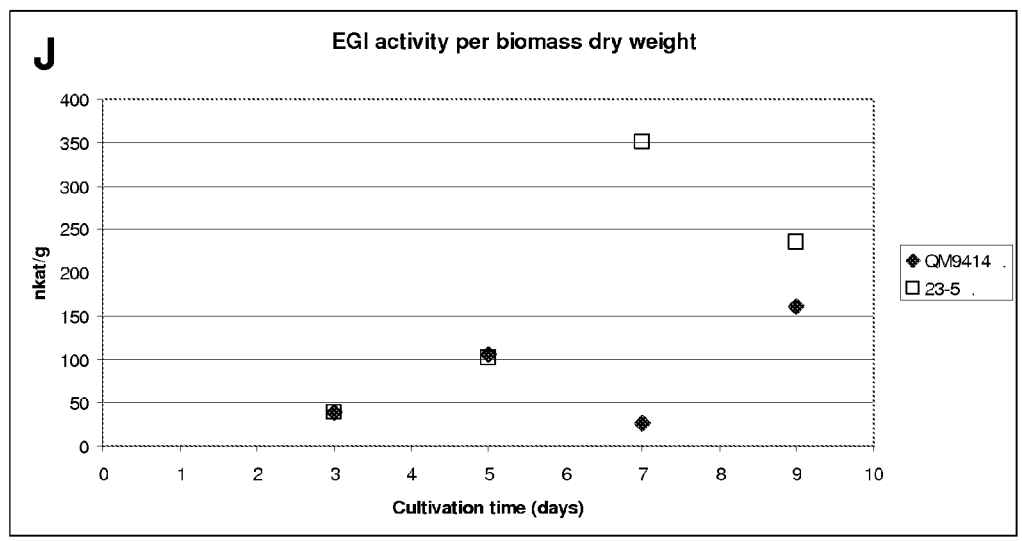
Figure 3:
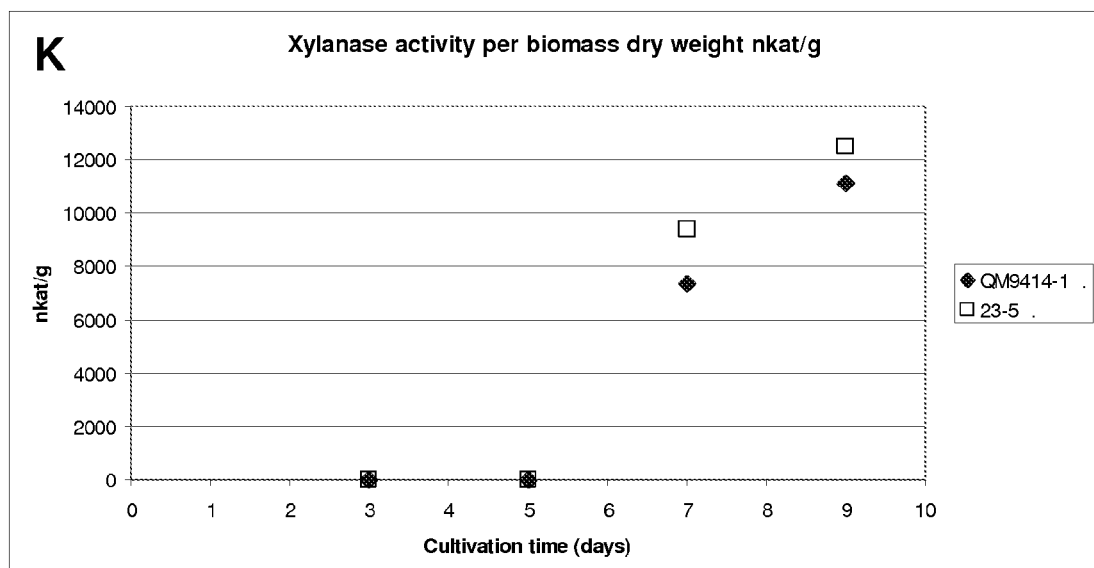

The effect of gene tre41573 (FIG. 3), represented by SEQ ID NO:3, was exemplified by constructing strain *T. reesei* 23-5 overexpressing the gene. The overexpression of this gene caused increased production of cellulase activity, measured as total Mulac, CBHI or EGI activity, increased production of hemicellulase activity, measured as xylanase activity, and increased production of total extracellular protein as compared to the parent host. The overexpression of gene tre41573 can be used in particular to increase cellulase or hemicellulase production, or the production of other secreted proteins. In addition, production of various heterologous proteins under the promoters of cellulase or hemicellulase genes (or similarly regulated promoters) can be produced at higher level by the strains overexpressing the gene as compared to the parent host strain.

Figure 4:
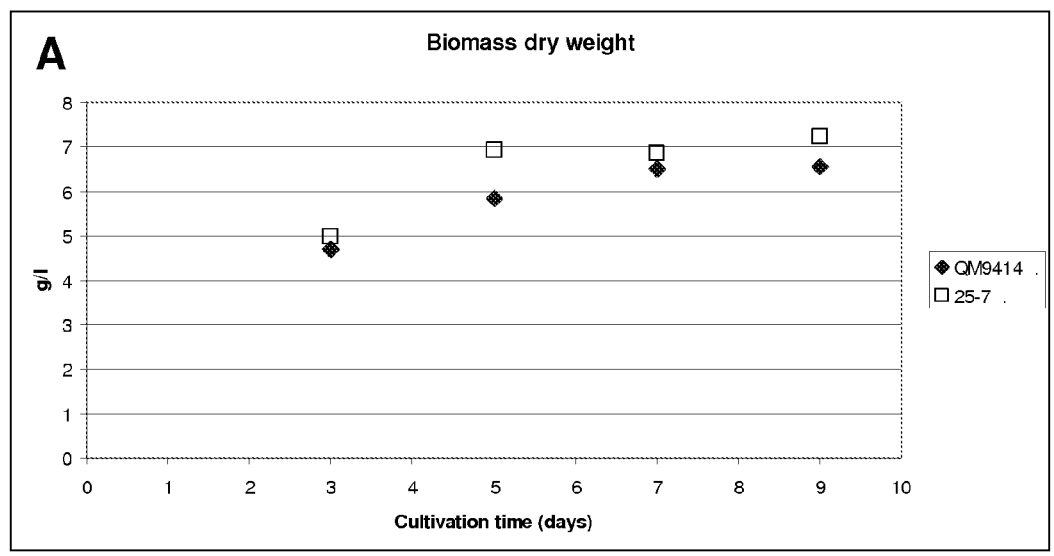
Figure 4:
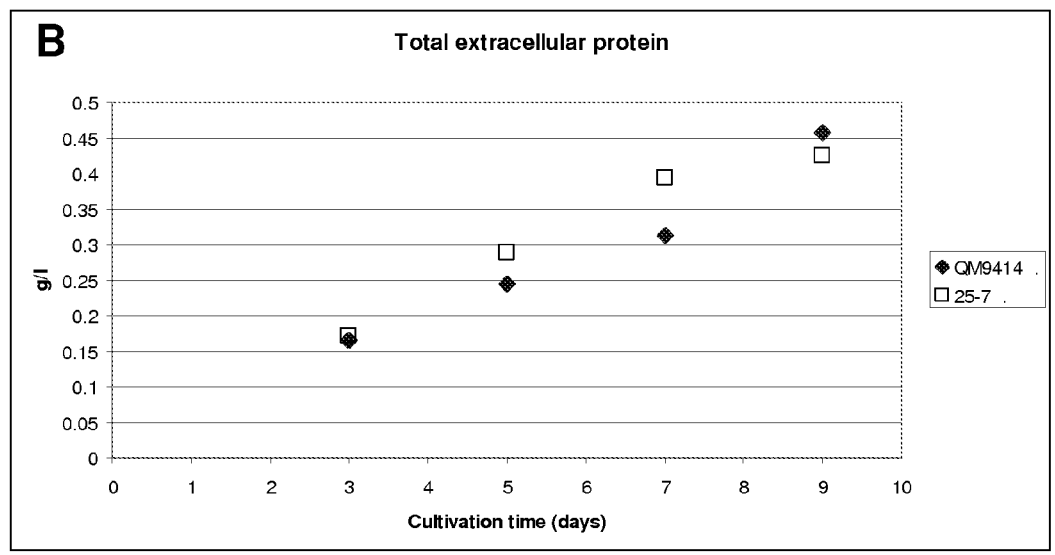
Figure 4:
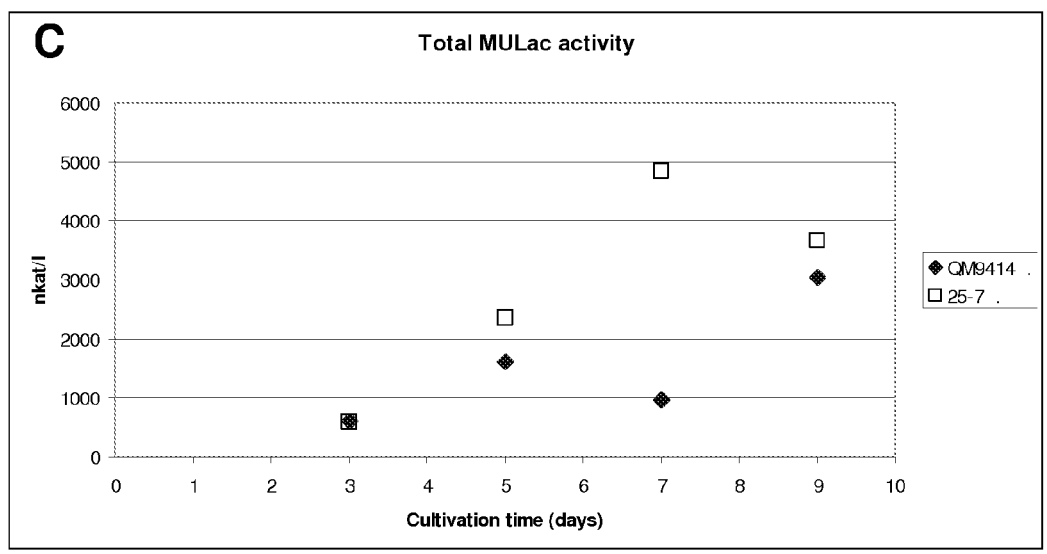
Figure 4:
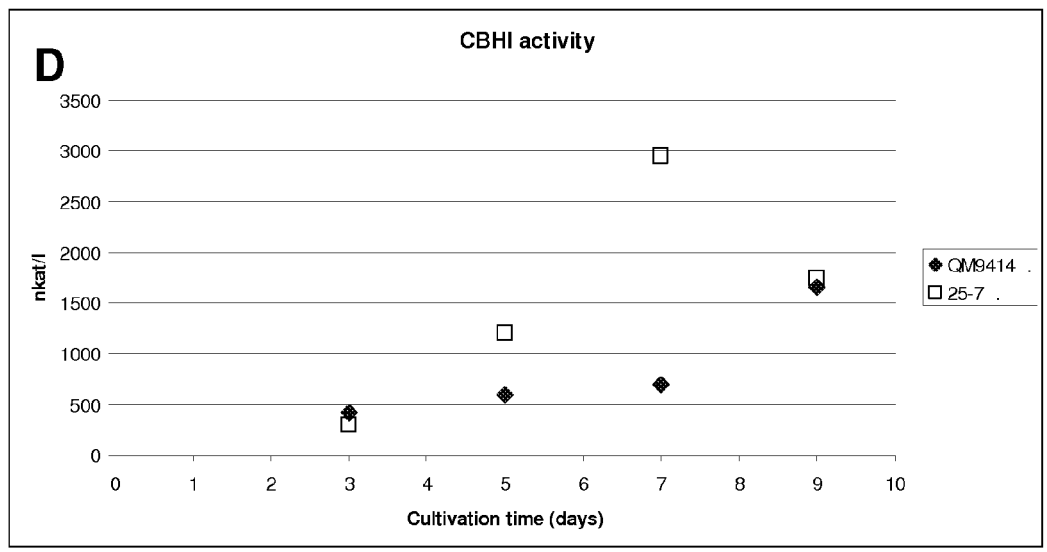
Figure 4:
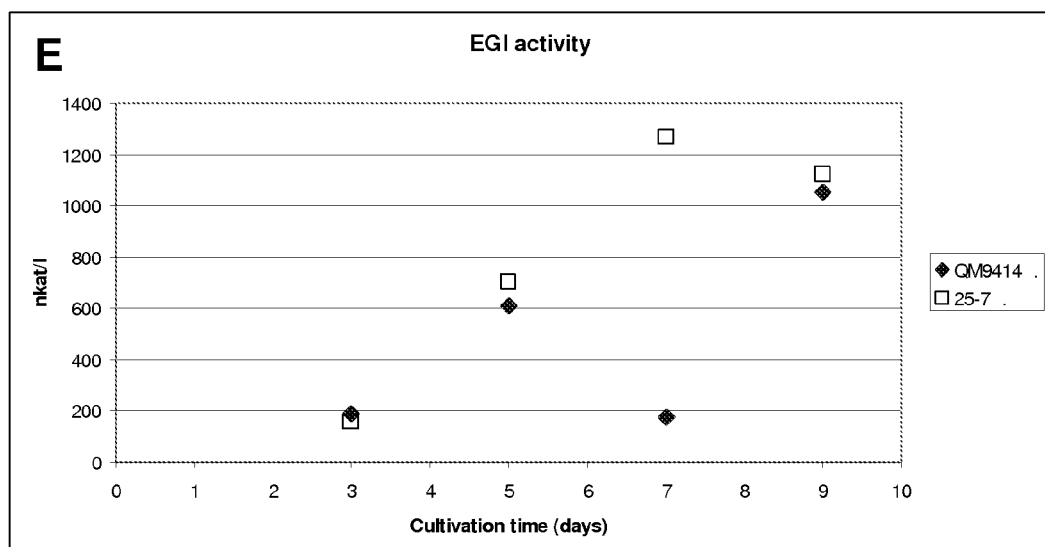
Figure 4:
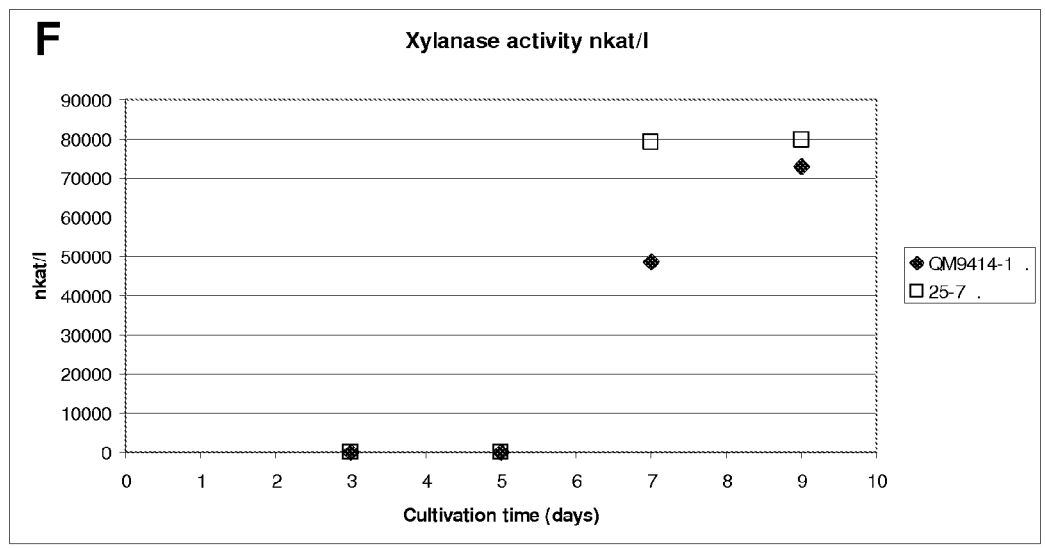
Figure 4:
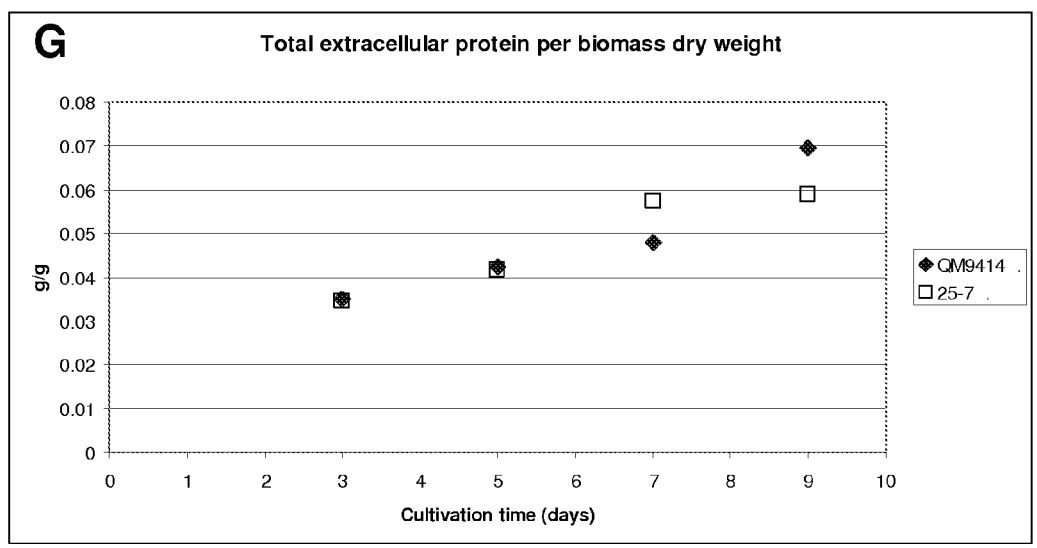
Figure 4:
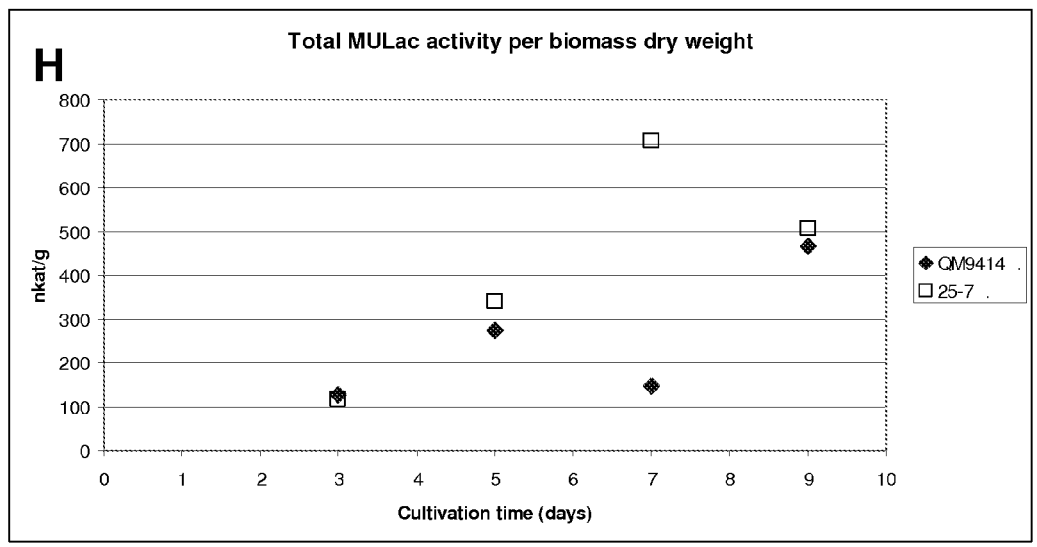
Figure 4:
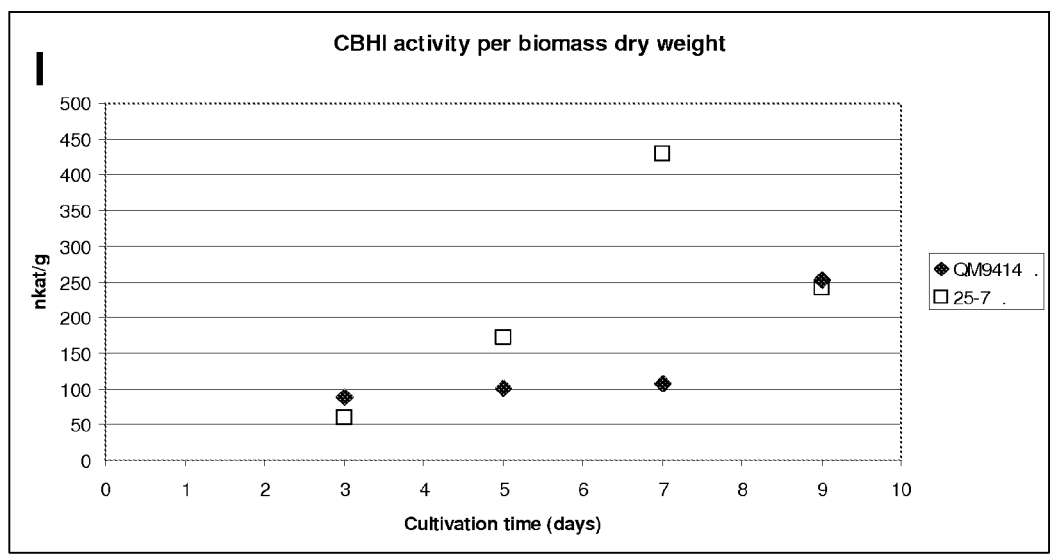
Figure 4:
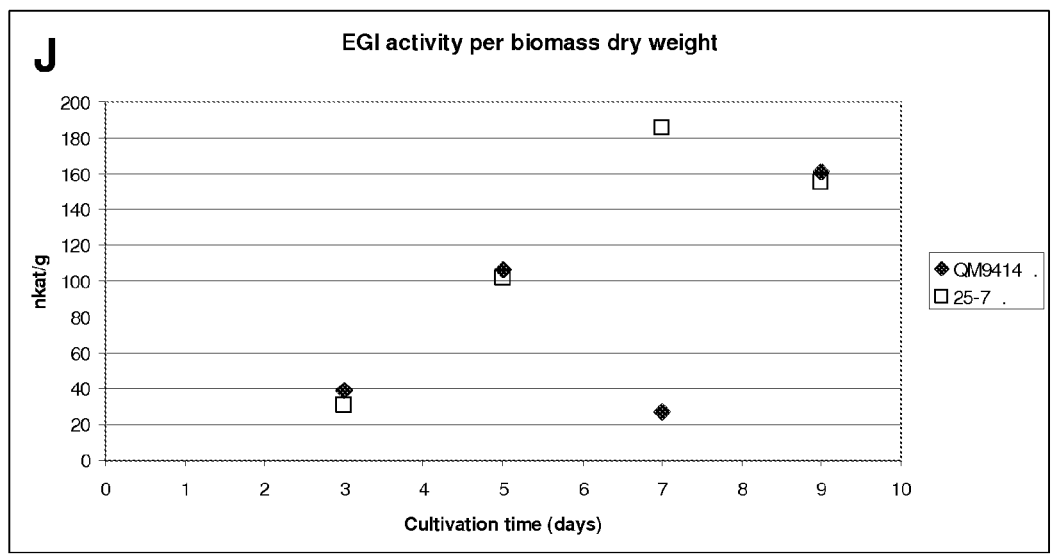
Figure 4:
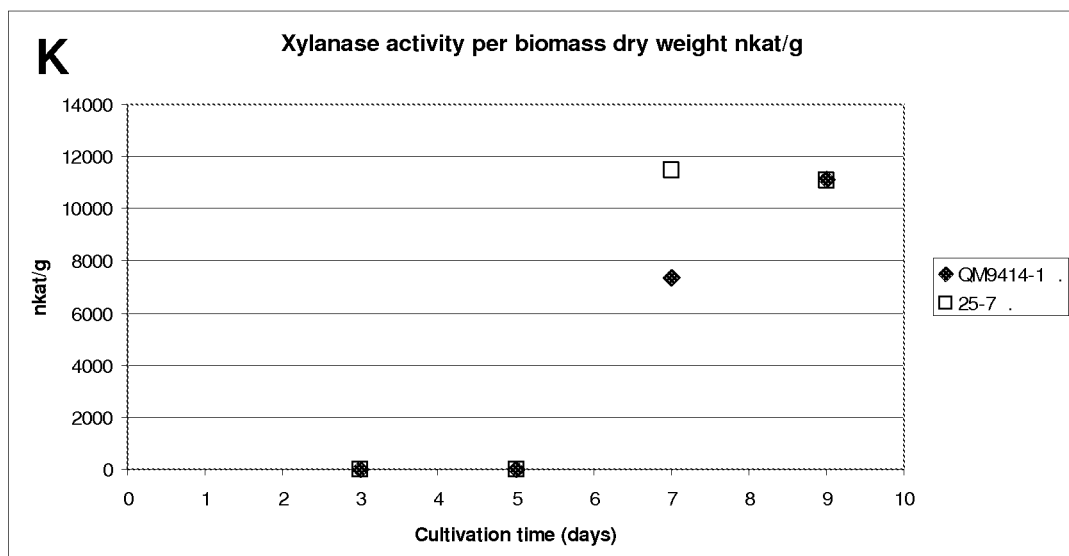

The effect of gene tre74765 (FIG. 4), represented by SEQ ID NO:4, was exemplified by constructing strain *T. reesei* 25-7 overexpressing the gene. The overexpression of this gene caused increased production of cellulase activity, measured as total Mulac activity, CBHI activity or EGI activity, and increased production hemicellulase activity, measured as xylanase activity, as compared to the parent host. The overexpression of the gene had also slightly positive effect on the total extracellular protein produced. The protein production process of the modified host was faster compared to the parent host. The overexpression of gene tre74765 can be used in particular to increase cellulase or hemicellulase production, or the production of other secreted proteins. In addition, production of various heterologous proteins under the promoters of cellulase or hemicellulase genes (or similarly regulated promoters) can be produced at higher level by the strains overexpressing the gene as compared to the parent host strain. By overexpressing gene tre123668 it is possible to make the protein production process faster.

Figure 5:
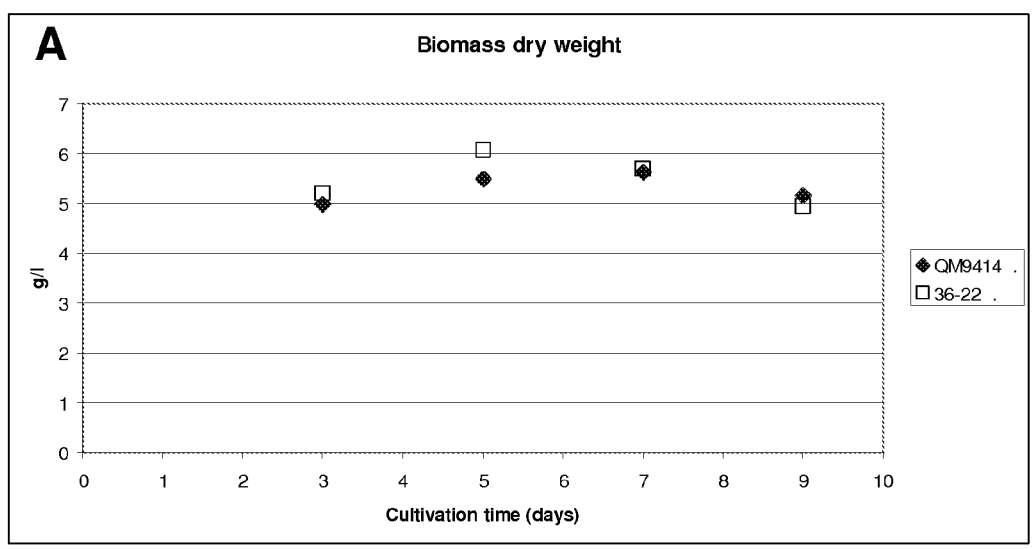
Figure 5:
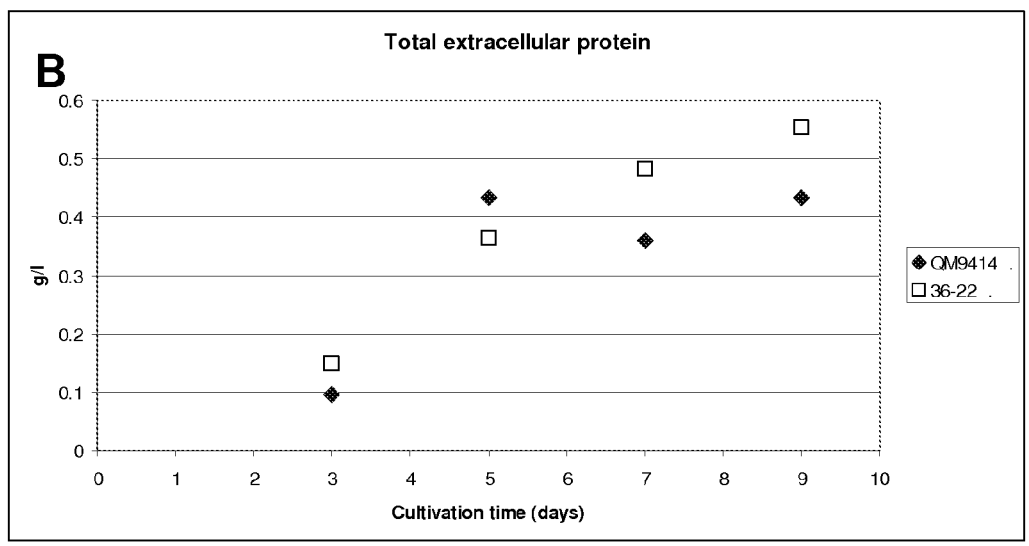
Figure 5:
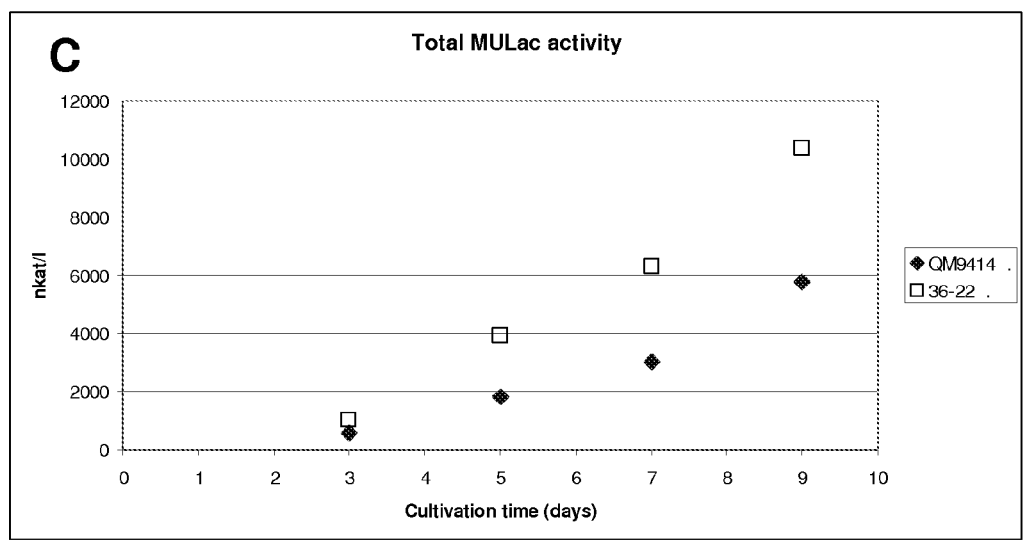
Figure 5:
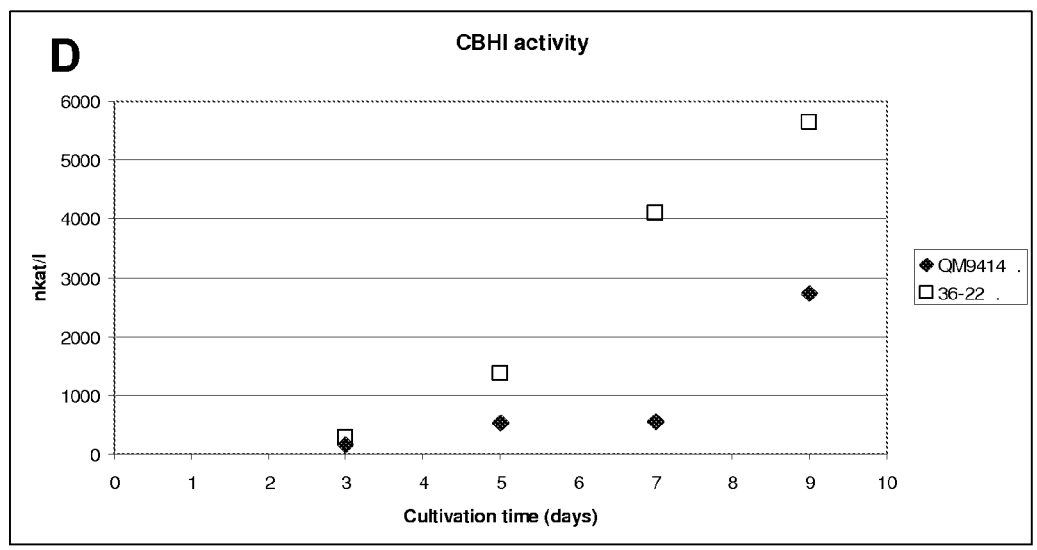
Figure 5:
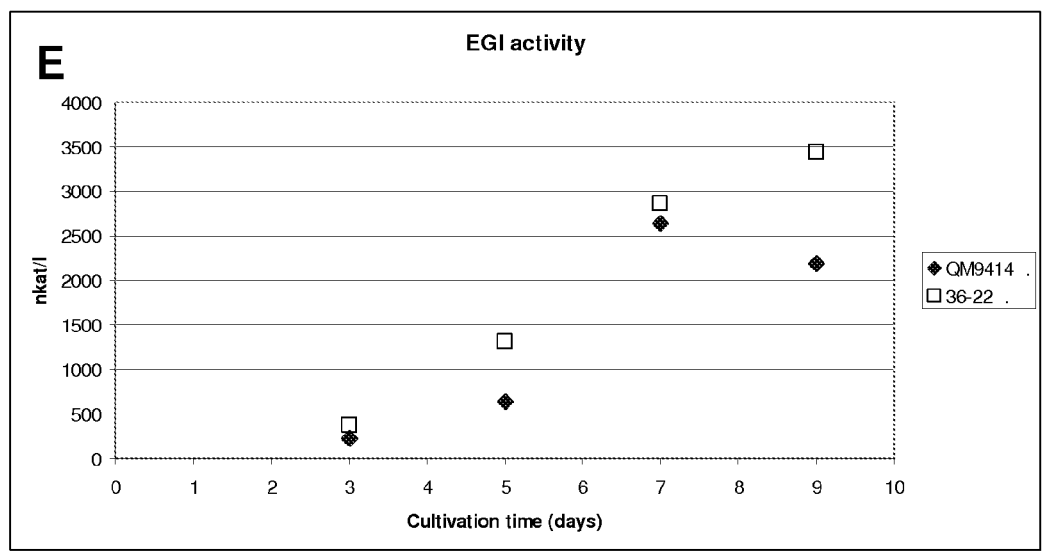
Figure 5:
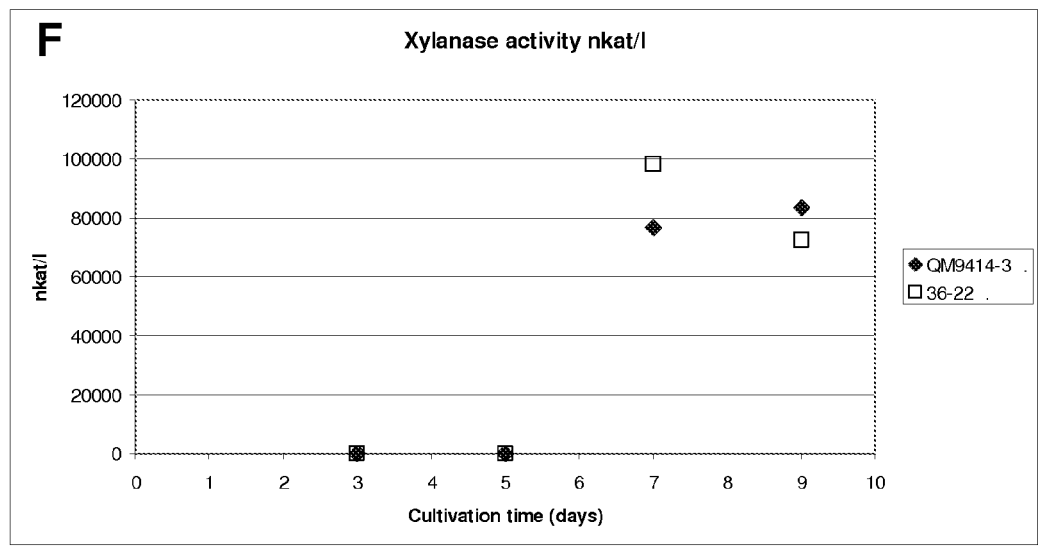
Figure 5:
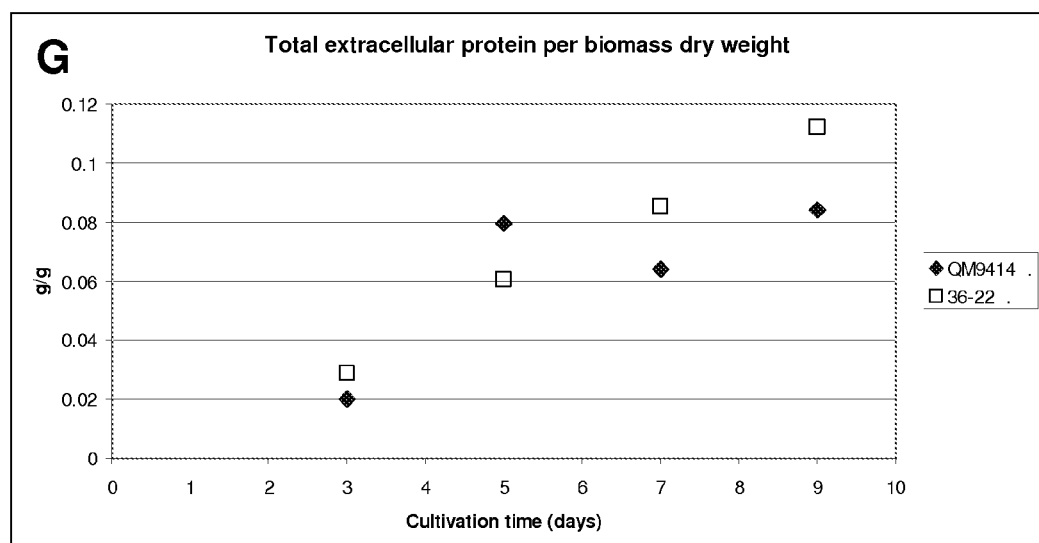
Figure 5:
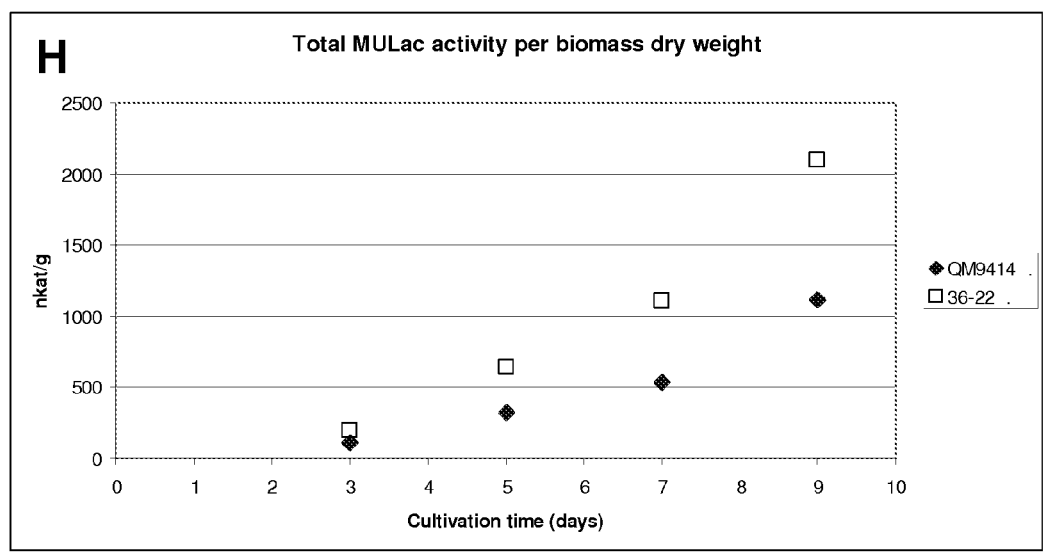
Figure 5:
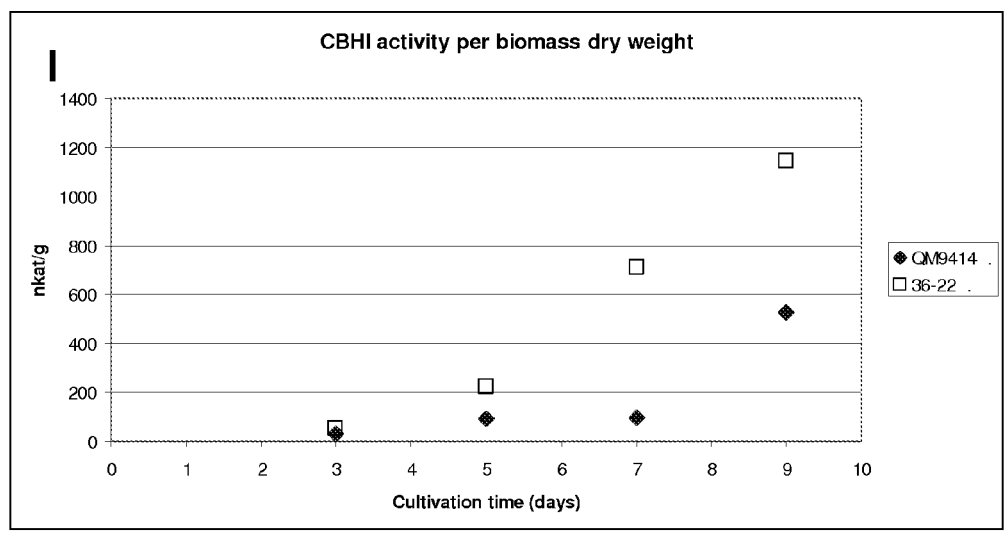
Figure 5:
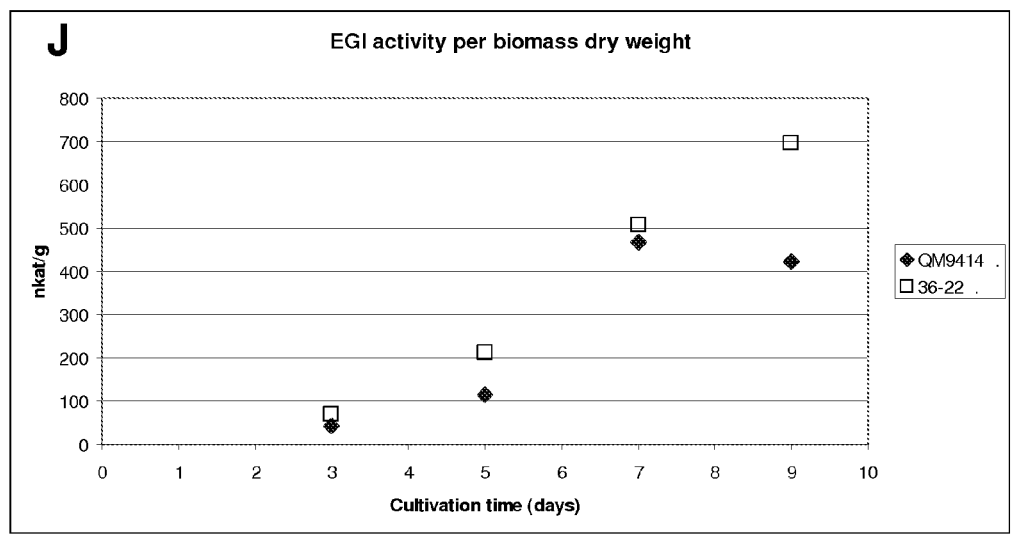
Figure 5:
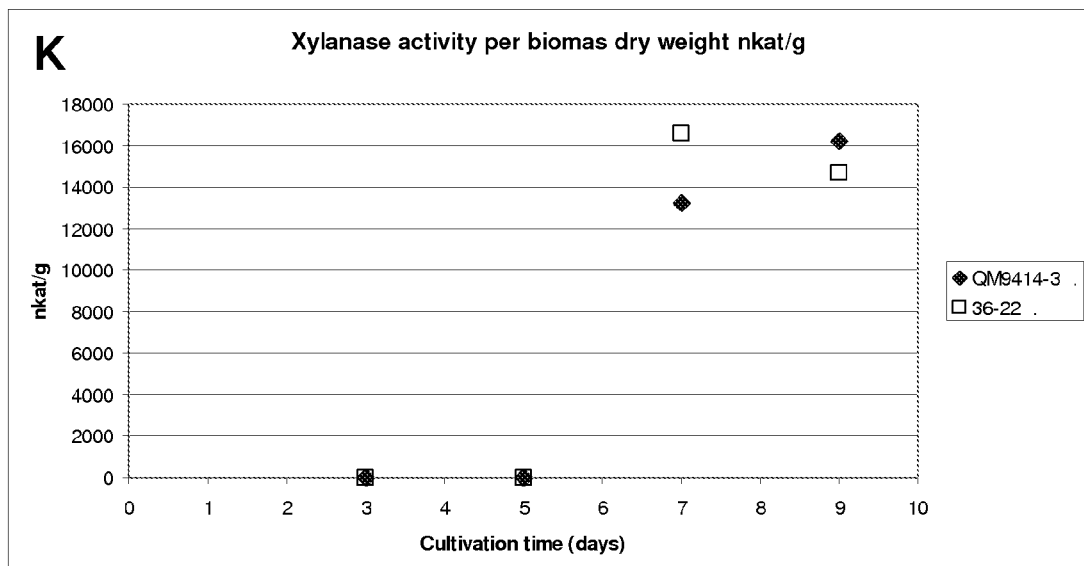
Figure 6A:
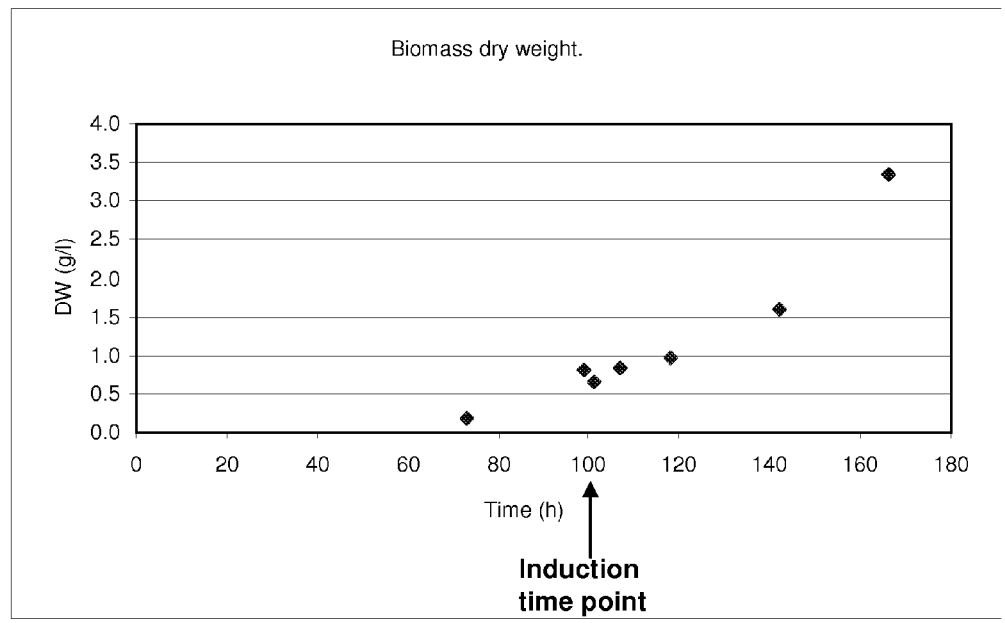
FIG. 6A Biomass (g/l) in *T. reesei* precultures before induction of hydrolytic enzyme production and in the uninduced control cultures at the sampling time points of the induction experiment.
Figure 6B:
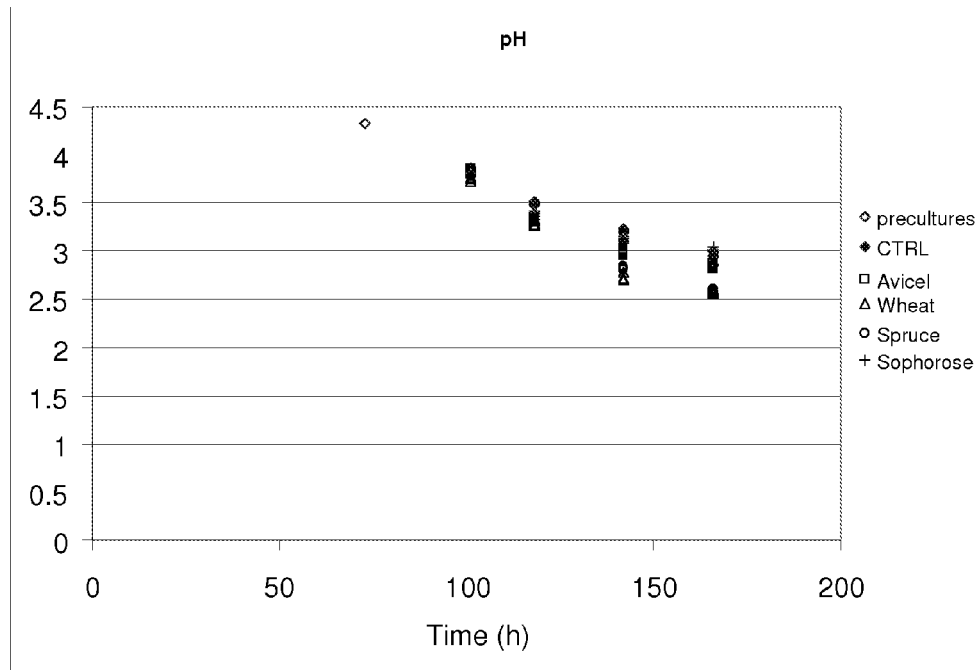
FIG. 6B pH of the *T. reesei* cultures induced either with Avicel, spruce, wheat straw or sophorose, as well as the precultures before induction and the uninduced control cultures.

The effect of gene tre64608 (FIG. 5), represented by SEQ ID NO:5, was exemplified by constructing strain *T. reesei* 36-22 overexpressing the gene. The overexpression of this gene caused increased cellulase production measured as total Mulac activity, CBHI activity and EGI activity. In particular CBHI activity was increased compared to the parent host. The overexpression of the gene had also slightly positive effect on the production of hemicellulase activity, measured as xylanase activity, and production of total extracellular protein. The overexpression of gene tre64608 can be used to increase cellulase or hemicellulase production, or the production of other secreted proteins. In addition, production of various heterologous proteins under the promoters of cellulase or hemicellulase genes (or similarly regulated promoters) can be produced at higher level by the strains overexpressing the gene as compared to the parent host strain.

The effect of the genes as described herein has been exemplified by overexpressing them in *Trichoderma*. The strain was *T. reesei* QM9414 (ATCC 26921), which is generally available to the public.

Total Mulac is measured as enzyme activity against Mulac substrate measuring activities of CBHI, EGI, and BGL.

EGI has been measured as enzyme activity against Mulac in the presence of glucose, to inhibit BGLI, and cellobiose, to inhibit the activity of CBHI.

CBHI has been measured as enzyme activity against Mulac obtained by subtracting the activity measured in the presence of glucose and cellobiose from the activity measured in the presence of glucose and in the absence of cellobiose.

The methods for determining cellulase activities has been described in Bailey and Tahtiharju, 2003; Collen et al., 2005; van Tilbeurgh et al., 1982, 1985, 1988.

Examples

Example 1

Cultivation of *Trichoderma reesei* for Transcriptome Analysis to Study the Cellular Responses During Induction of Hydrolytic Enzyme Production Cultivation Procedure

*Trichoderma reesei* Rut-C30 (ATCC56765) was cultivated in shake flasks in medium containing 7.6 g/l $(NH_4)_2SO_4$, 15.0 g/l $KH_2PO_4$, 2.4 mM $MgSO_4.7H_2O$, 4.1 mM $CaCl_2.H_2O$, 3.7 mg/l $CoCl_2$, 5 mg/l $FeSO_4.7H_2O$, 1.4 mg/l $ZnSO_4.7H_2O$, 1.6 mg/l $MnSO_4.7H_2O$, and 10 g/l sorbitol. pH of the medium was adjusted to 4.8 by addition of KOH. The cultures were inoculated with $8 \times 10^7$ spores/200 ml medium and grown for 4 days in conical flasks at 28° C. with shaking at 250 rpm. For induction of the hydrolytic enzyme production, the cultures were combined and aliquots of the combined culture transferred to flasks containing inducing medium (200 ml of the culture per 90 ml of the inducing medium). The composition of the inducing medium was as described above except for containing 2 g/l sorbitol and supplemented either with Avicel cellulose, pretreated wheat straw, pretreated spruce or sophorose. Uninduced control cultures were treated similarly except that no supplement was used in the inducing medium. The concentrations of the inducing substances were 1% (w/v) of Avicel, wheat or spruce or 0.7 mM sophorose. Pretreatment of spruce and wheat straw was done using steam explosion, followed by washing steps. The fibrous fraction of the material was used for the induction.

Collection of Samples and Sample Treatment

Samples for analysis of biomass production, pH of the culture supernatant, and for RNA isolation were collected at different time points during the pre-cultivation step as well as from the combined culture before induction. After addition of the inducing substances the cultures were sampled for pH measurement and RNA isolation; biomass formation was measured only from separate uninduced control flasks reserved for the purpose. The sampling time points of the induced cultures were 0 h, 6 h, 17 h, and 41 h after the onset of induction. Biomass dry weight was measured by filtering and drying mycelium samples at 105° C. to constant weight (24 h). For RNA isolation mycelium samples of 50 ml were filtered, washed with equal volume of 0.7% (w/v) NaCl, frozen immediately in liquid nitrogen, and stored at −80° C. Total RNA was isolated using the Trizol™ Reagent (Gibco BRL) essentially according to manufacturer's instructions, and purified further by column purification (Qiagen, manufacturer's instructions). cDNA was synthesised from the purified RNA, followed by fluorescent labelling and expression microarray analysis using custom oligonucleotide microarrays by Roche NimbleGen, Inc. The design for the microarray probes and slides was done according to JGI *T. reesei* genome version v2.0.

Monitoring of the Cultures

Figure 7A:
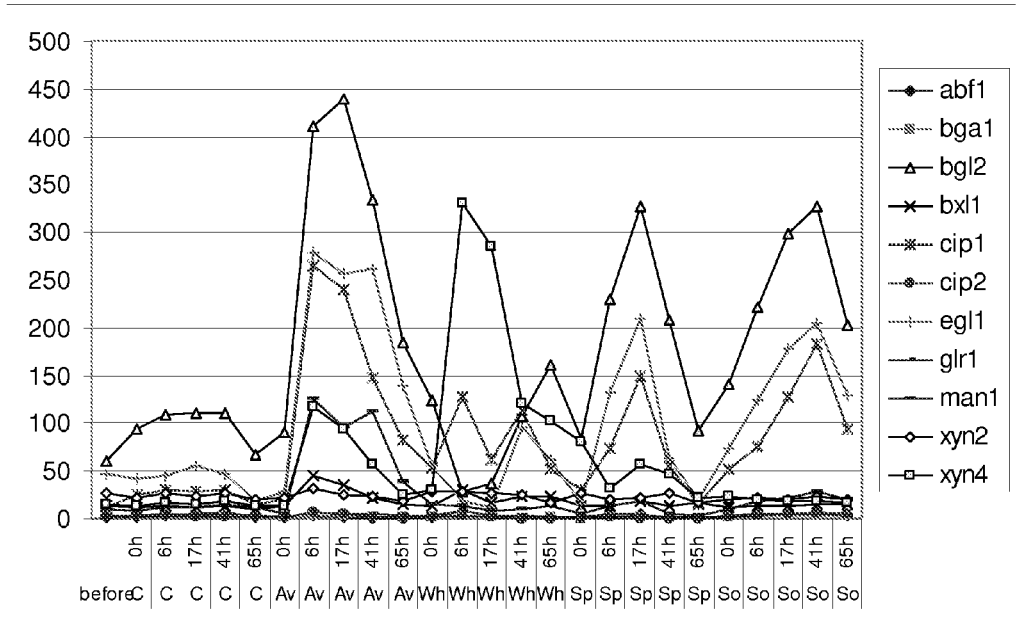
FIG. 7A. Transcript levels of a set of known genes encoding hydrolytic enzymes during an induction experiment: abf1 (arabinofuranosidase 1), bga1 (beta-galactosidase 1), bgl1 (beta-glucosidae 1), bxl1 (beta-xylosidase 1), cip1 (cellulose-binding), cip2 ( ) egl1 (endoglucanase 1), glr1 (glucuronidase 1), man1, xyn2 and xyn4.
Figure 7B:
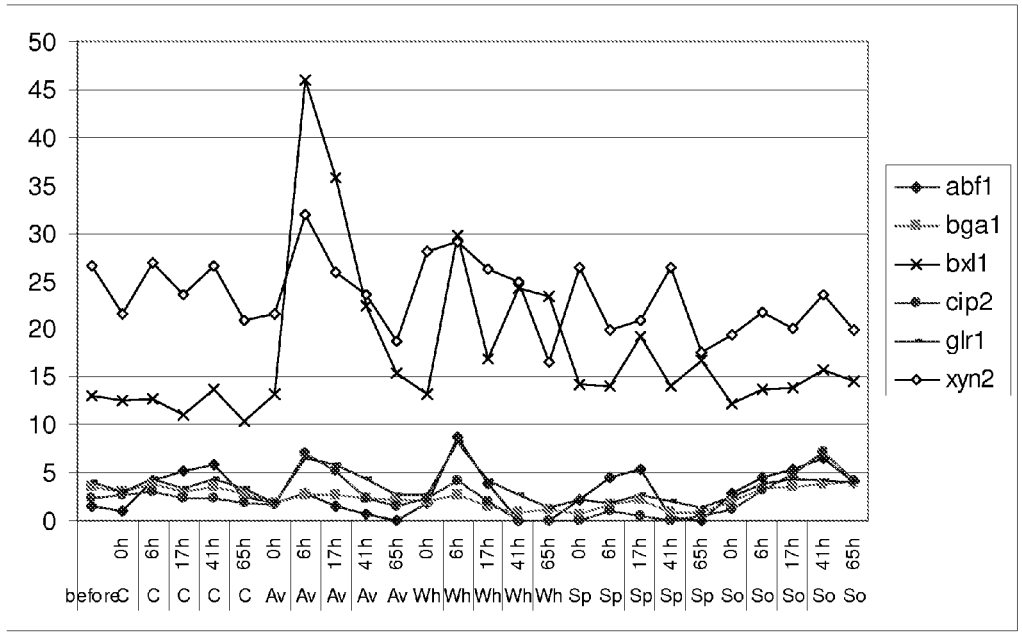
FIG. 7B Transcript levels of a set of known genes encoding hydrolytic enzymes during an induction experiment: abf1 (arabinofuranosidase 1), bga1 (beta-galactosidase 1), bxl1 (beta-xylosidase 1), cip2 ( ), glr1 (glucuronidase 1), and xyn2.

During the precultivation stage the progress of the cultivations was monitored by analysis of biomass formation and change of pH in the culture supernatant. After the onset of the induction biomass formation was only measured from uninduced control cultures specifically dedicated for the purpose, since the insoluble material in the inducing media could not be separated from fungal biomass. pH was measured from all the cultures throughout the cultivation procedure. Biomass dry weight (g/l) in the precultures before induction and in the uninduced control cultures are shown in FIG. 7A and pH of the cultures in FIG. 7B. The biomass and pH data show that, at the induction time point 100 h, the cultivations were actively growing and growth continued during the induction time period in the control cultures. The extent of pH decrease in the cultures during time suggest equal growth characteristics of the replicate cultures. No significant difference was detected between the uninduced and sophorose induced cultures either. In cultures with Avicel, the pH decreased slightly faster as compared to the uninduced culture, and the cultures with spruce and wheat showed fastest decrease in the pH, the difference being, however, relatively small.

Example 2

TRAC Analysis of a Selected Set of Genes Encoding Hydrolytic Enzymes

In order to select the optimal time points of the induction experiment for the expression microarray analysis, transcription levels of a set of known genes encoding hydrolytic enzymes were analysed using TRAC method. The relative expression levels are shown for abf1 (arabinofuranosidase 1), bga1 (beta-galactosidase 1), bgl1 (beta-glucosidae 1), bxl1 (beta-xylosidase 1), cip1 (cellulose-binding), cip2 ( ) egl1 (endoglucanase 1), glr1 (glucuronidase 1), man1, xyn2 and xyn4. Clear induction was detected for majority of the genes at the time points 6 h and 17 h, and also at 41 h of the sophorose cultures, and these time points were selected for the microarray analysis. The transcript levels detected by the TRAC analysis are shown in FIG. 8A and FIG. 8B.

Example 3

Expression Microarray Analysis of the Induced Cultures

The cultures induced either with Avicel, sophorose, pretreated wheat straw or pretreated spruce were subjected to microarray expression analysis. The time points 0 h, 6 h, 17, and 41 h of the uninduced and sophorose induced cultures were used for the analysis, and the time points 0 h, 6 h and 17 h were selected for the Avicel, wheat and spruce induced cultures. The microarray analysis was done using custom oligonucleotide microarrays by Roche NimbleGen, Inc. The design for the microarray probes and slides was done according to JGI *T. reesei* genome version v2.0. Raw microarray data was analysed using R and the Bioconductor packages Oligo, Limma and Mfuzz.

The analysis showed co-expression of a group of genes together with cellulase or hemicellulase genes. These genes included novel previously not described genes with sequence domains typical to genes for regulatory proteins, genes for transcription factors and proteins involved in histone modification and chromatin remodelling. In order to evaluate the effect of these genes on protein production, and specifically production of hydrolytic enzymes, like cellulases and hemicellulases, a set of these genes were cloned and overexpressed in *T. reesei* QM9414 (ATCC 26921). The selected genes had a significantly higher expression at least in three of the inducing conditions studied as compared to the uninduced cultures at the same time point, or that the expression profile of the genes was similar to the expression profiles of known hemicellulase or cellulase genes (according to M fuzz clustering of the expression data). The selected genes with their corresponding protein identity number, predicted functional prediction based on the sequence domains, and information on their induction in the presence of different inducing substances at different time points of the induction experiment are listed in Table 3.

The information provided on the genes include the ID number according to JGI genome version 2.0, predicted function of the gene based on the sequence data, and data on induction of the gene in the presence of different inducers (Avicel, pretreated wheat straw, pretreated spruce or sophorose) at different induction time points. Statistically significant induction (higher expression level as compared to the uninduced control cultures at the same time point) in the Avicel, Spruce, Wheat or Sophorose induced cultures at the time points 0 h, 6 h, 17 h, or 41 h is indicated by "1", and statistically significant reduction in the expression level by "−1".

TABLE 3

The induced genes encoding putative regulatory factors and selected for overexpression in *T. reesei*.

| | | | Inducer | | | | | | | |
|---|---|---|---|---|---|---|---|---|---|---|
| | | | Avicel | Avicel | Avicel | Wheat | Wheat | Wheat | Spruce | Spruce |
| | | | | | | | Time (h) | | | |
| Gene ID | Class | Extension | 0 h | 6 h | 17 h | 0 h | 6 h | 17 h | 0 h | 6 h |
| TRIRE0077513 | Regulation | Transcription factor | 0 | 1 | 1 | 0 | 0 | −1 | 0 | 1 |
| TRIRE0080291 | Regulation | Transcription factor | 0 | 0 | 1 | 0 | 1 | 1 | 0 | 1 |
| TRIRE0041573 | Regulation | Transcription factor | 0 | 0 | 1 | 0 | 1 | 0 | 0 | 1 |

TABLE 3-continued

The induced genes encoding putative regulatory factors and selected for overexpression in *T. reesei*.

| | | | | | | | | |
|---|---|---|---|---|---|---|---|---|
| TRIRE0074765 | Regulation | Bromodomain, BTB/POZ | 0 | 1 | 1 | 0 | 1 | 1 | 0 | 1 |
| TRIRE0064608 | Regulation | G-protein beta WD-40 repeat | 0 | 0 | 0 | 0 | 0 | 0 | 0 | 0 |

| | | | Inducer | | | | |
|---|---|---|---|---|---|---|---|
| | | | Spruce | Sophorose | Sophorose Time (h) | Sophorose | Sophorose |
| Gene ID | Class | Extension | 17 h | 0 h | 6 h | 17 h | 41 h |
| TRIRE0077513 | Regulation | Transcription factor | 1 | 0 | 1 | 1 | 1 |
| TRIRE0080291 | Regulation | Transcription factor | 1 | 0 | 0 | 1 | 0 |
| TRIRE0041573 | Regulation | Transcription factor | 0 | 0 | 0 | 0 | 0 |
| TRIRE0074765 | Regulation | Bromodomain, BTB/POZ | 1 | 0 | 1 | 1 | 0 |
| TRIRE0064608 | Regulation | G-protein beta WD-40 repeat | 0 | 0 | 0 | 0 | 0 |

Example 4

The primers used for amplification of the genes from *T. reesei* QM6a (CBS383.78) genome were as follows:

The 5'end primer contained a general part consisting of four 5'terminal G's, 25nt attB1 site (ACAAGTTTGTACAAAAAAGCAGGCT) (SEQ ID NO:6) and a 8 nt region upsam from start codon of cbh1 gene (TGCGCATC), altogether forming the sequence GGGGACAAGTTTGTACAAAAAAGCAGGCTTGCGCATC (SEQ ID NO:7).

The general component of the oligo was followed by gene specific sequence corresponding to the 5'end of the gene.

The 3'end primer contained four 5'terminal G's, 25nt attB2 site (ACCACTTTGTACAAGAAAGCTGGGT) (SEQ ID NO:8) and the nucleotides CTTA followed by the gene specific sequence corresponding to the 3'end of the gene.

The gene specific part of the primers were designed based on the ORF prediction in the JGI genome version v2.0, or in some cases, as indicated below, according to the JGI genome version v1.2. The primers used for amplification of the genes using genomic *T. reesei* DNA as a template were the following:

pMH15 77513
(SEQ ID NO: 9)
5'GGGGACAAGTTTGTACAAAAAAGCAGGCTTGCGCATCATGCTGCGCTACTCCCCCGTCT pMH15 77513
(SEQ ID NO: 10)
3'GGGGACCACTTTGTACAAGAAAGCTGGGTTTTAGCCAACAACGGTAGTGGA pMH20 80291
(SEQ ID NO: 11)
5'GGGGACAAGTTTGTACAAAAAAGCAGGCTTGCGCATCATGGGCCGGCAACCGAGACAAC pMH20 80291
(SEQ ID NO: 12)
3'GGGGACCACTTTGTACAAGAAAGCTGGGTATTATATAAACGGGCATCAAT pMH23 41573
(SEQ ID NO: 13)
5'GGGGACAAGTTTGTACAAAAAAGCAGGCTTGCGCATCATGCTGAGTCAGAGTCCTCGAGC pMH23 41573
(SEQ ID NO 14)
3'GGGGACCACITTGTACAAGAAAGCTGGGTCCTAGGATTGACCAGGCCGTG pMH25 74765
(SEQ ID NO: 15)
5'GGGGACAAGTTTGTACAAAAAAGCAGGCTTGCGCATCATGACTTCTGAAGCCCCCTCTC pMH25 74765
(SEQ ID NO: 16)
3'GGGGACCACTTTGTACAAGAAAGCTGGGTCCTACTCGCCCTCTTCGCCTC pMH36 64608
(SEQ ID NO: 17)
5'GGGGACAAGTTTGTACAAAAAAGCAGGCTTGCGCATCATGTCCAGATTCTGTCCGCT pMH36 64608
(SEQ ID NO: 18)
3'GGGGACCACTTTGTACAAGAAAGCTGGGTGCATCAATAGGCCGTATCAGAG

PCR amplification reaction using the primers mentioned above resulted in DNA fragments containing the gene specific sequences described below inserted between the 5' and 3' terminal sequences originating from the general parts of the primers.

Example 5

Figure 8:
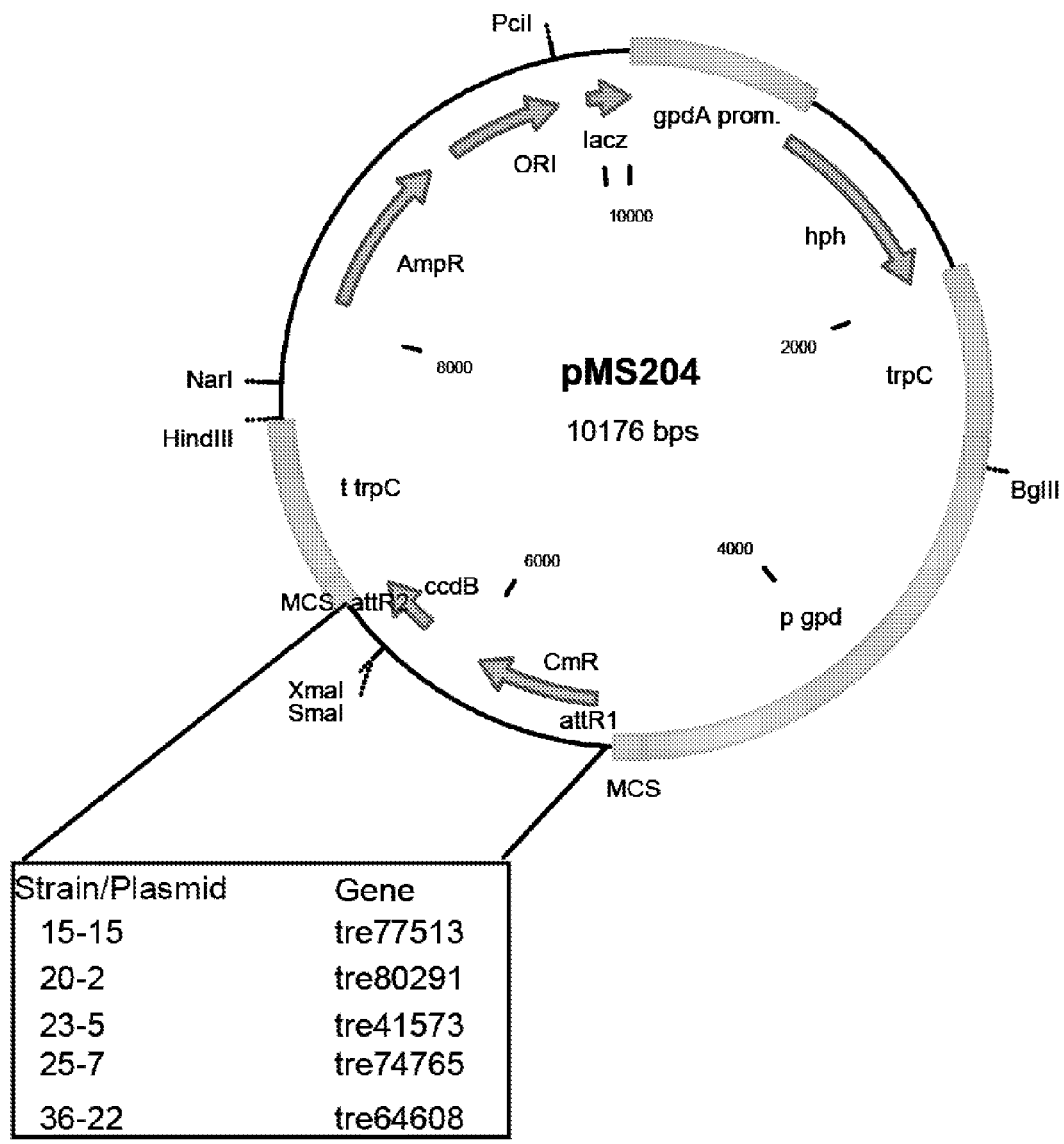
FIG. 8 Schematic view of the plasmid constructs made for transforming the strain *T. reesei* QM9414 and generating the strains overexpressing the genes encoding putative regulatory factors. The gene is inserted in the plasmid vector by replacing the region between attR1 attR2 sites containing the genes ccdB and CmR with the gene specific sequences. The names of the plasmids and the corresponding *T. reesei* strains obtained by transformation and the corresponding gene inserted in the plasmid are listed.

Construction of *T. reesei* Strains Overexpressing the Regulatory Genes Selected Based on the Transcriptome Data from the Induction Experiment on Avicel, Wheat, Spruce or Sophorose Containing Media The genes encoding putative regulatory factors co-expressed with known cellulase or hemicellulase genes were amplified by PCR from the *Trichoderma* genome (*T. reesei* QM6a; CBS383.78) and cloned into an expression vector which was then transformed into *T. reesei* QM9414. The transformants were selected based on function of the AmdS selection marker gene present in the expression cassette, transformants were purified from colonies originating from single spores, and the integration of the expression cassette into the genome was confirmed by PCR amplification of the cassette. Schematic view of the plasmids used for transformation is shown in FIG. 8.

Example 6

Cultivation of the *T. reesei* Strains Overexpressing the Putative Regulatory Factors, and Analysis of the Cultures for Growth and Protein Production The modified strains overexpressing genes encoding the putative regulatory factors were cultivated in shake flasks on medium containing 7.6 g/l $(NH_4)_2SO_4$, 15.0 g/l $KH_2PO_4$, 2.4 mM $MgSO_4.7H_2O$, 4.1 mM $CaCl_2.H_2O$, 3.7 mg/l $CoCl_2$, 5 mg/l $FeSO_4.7H_2O$, 1.4 mg/l $ZnSO_4.7H_2O$, 1.6 mg/l $MnSO_4.7H_2O$ and supplemented with 4% lactose and 2% spent grain extract. The cultures were analysed for growth and protein production, including assays for cellulase and hemicellulase activity. Cellulase activity was measured using 4-methylumbelliferyl-β-D-lactoside (MULac) as a substrate. The MULac can be used for measurement of combined activities of CBHI, EGI and BGL in *T. reesei* cultures (Bailey and Tahtiharju, 2003; Collen et al., 2005; van Tilbeurgh et al., 1982, 1985, 1988. Using a modified method MULac substrate can used also to measure the activities of CBHI and EGI specifically (Bailey and Tahtiharju, 2003; Collen et al., 2005; van Tilbeurgh et al., 1982, 1985, 1988). Xylanase activity was measured using birch xylan as a substrate (Bailey M. J., Biely P., and Poutanen, K., (1992) Interlaboratory testing of methods for assay of xylanase activity. J. Biotechnol. 23: 257-270). For the results on protein production in the cultures of the modified strains and the parental strain *T. reesei* QM9414, see the FIGS. 1-5.

Example 7

The closest homologue of a gene in another fungal species can be identified e.g. based on homology searches against genome databases using programs such as Blast. The homology searches can be done using either the nucleotide sequence of the gene or the amino acid sequence of the translated gene as a query. Information on the closest homologue of the gene can be obtained in any organism with a sequenced genome. Complete genome sequences are available for homology searches for a multitude of fungal species, and the number of fully sequenced fungal organisms is still increasing.

In this example, the translated sequences of the ORFs of the *T. reesei* genes tre77513, tre80291, tre41573, tre74765 and tre64608 were subjected to BLASTP homology search against protein sequence databases of a set of fungal species. The translated sequences of the *T. reesei* ORFs were according to JGI (Joint Genome Institute) genome version 2.0, JGI genome version 1.2. The corresponding protein IDs in the JGI database used in the homoplogy search were as follows:

| Gene | Protein ID |
| --- | --- |
| tre77513 | 77513, JGI genome version 2.0 |
| tre80291 | 80291, JGI genome version 2.0 |
| tre41573 | 74896 (an alternative ORF model for 41573), JGI genome version 2.0 |
| tre74765 | 74765, JGI genome version 2.0 |
| tre64608 | 36860, JGI genome version 1.2 |

The search was carried out using the fungal genome BLAST databases at NCBI containing completed genome sequence and whole genome shotgun sequence data with the corresponding protein sequences of a large number of fungal species. The databases used in the search in this example were:

Completed *Aspergillus fumigatus* proteins;

Completed *Aspergillus nidulans* FGSC A4 proteins;

Completed *Aspergillus terreus* proteins;

Completed *Chaetomium globosum* CBS 148.51 proteins;

Completed *Gibberella zeae* PH-1 proteins;

(The reference for the BLASTP 2.2.23+ program used: S. F. Altschul, T. L. Madden, A. A. Schaffer, J. Zhang, Z. Zhang, W. Miller, and D. J. Lipman (1997), "Gapped BLAST and PSI-BLAST: a new generation of protein database search programs", Nucleic Acids Res. 25:3389-3402. Reference for compositional score matrix adjustment: S. F. Altschul, J. C. Wootton, E. M. Gertz, R. Agarwala, A. Morgulis, A. A. Schaffer, and Y.-K. Yu (2005) "Protein database searches using compositionally adjusted substitution matrices", FEBS J. 272:5101-5109.).

The parameters used in the searches were as follows:

General Parameters:

Max target sequences: 100 (Maximum number of aligned sequences to display (the actual number of alignments may be greater than this)).

Short queries: Automatically adjust word size and other parameters to improve results for short queries.

Expect threshold: 10 (Expected number of chance matches in a random model)

Word size: 3 (The length of the seed that initiates an alignment)

Scoring Parameters:

Matrix: BLOSUM62 (Assigns a score for aligning pairs of residues, and determines overall alignment score)

Gap Costs: Existence: 11, Extension: 1 (Cost to create and extend a gap in an alignment)

Compositional adjustments: Conditional compositional score matrix adjustment (Matrix adjustment method to compensate for amino acid composition of sequences)

Filters and Masking:

Filter: Low complexity regions filter (Mask regions of low compositional complexity that may cause spurious or misleading results)

Table 4. shows examples of the closest homologues of the *T. reesei* genes in other fungal species obtained by the BLAST search: the closest homologue of tre77513 in *A. fumigatus*, tre80291 in *G. zeae*, tre41573 in *G. zeae*, tre74765 in *G. zeae* and tre64608 in *A. fumigatus*.

TABLE 4

Examples of the closest homologues of the *T. reesei* genes in selected fungal species based on the BLAST search

| Query sequence | Query sequence length (amino acids) | Hit sequence | Species | Blast Score | Blast E value | Identical amino acids per query length (%) | Identical amino acids/ length of the alignment | Identities in the alignment (%) | Alignment length/ query length (%) |
|---|---|---|---|---|---|---|---|---|---|
| translated tre77513 | 651 | ref\|XP_753007.1\| | *Aspergillus fumigatus* | 577 | 4.00E-164 | 52 | 336/653 | 51 | 100 |
| translated tre80291 | 728 | ref\|XP_384492.1\| | *Gibberella zeae* | 451 | 4.00E-126 | 37***) | 234/585 | 40 | 80 |
| translated tre41573*) | 330 | ref\|XP_390008.1\| | *Gibberella zeae* | 140 | 4.00E-33 | 41 | 135/225 | 60 | 68 |
| translated tre74765 | 445 | ref\|XP_389893.1\| | *Gibberella zeae* | 548 | 1.00E-155 | 61 | 270/413 | 65 | 93 |
| translated tre64608**) | 627 | ref\|XP_750677.1\| | *Aspergillus fumigatus* | 540 | 7E-153 | 48 | 302/576 | 52 | 92 |

*)The translated ORF according to ORF ID 74896, JGI genome version 2.0
**)The translated ORF according to ORF ID 36860, JGI genome version 1.2
***)the % of identical amino acids for 80291 is deduced from two separate aligned regions

The invention claimed is:

1. A method to genetically modify a *Trichoderma reese* host for improved protein production said method comprising:
  genetically modifying the host to overexpress with increased amount or activity, or to be deficient with reduced or lacking amount or activity, of gene tre77513 having nucleotide sequence according to SEQ ID NO:1, or a coding region of SEQ ID NO:1, said host being capable of increased or decreased production of cellulase, hemicellulase, other proteins involved in degradation of lignocellulosic material and/or other proteins as compared to the parental *Trichoderma reesei* strain.

2. The method according to claim 1, wherein the *Trichoderma reesei* host is genetically modified to overexpress gene tre77513 having nucleotide sequence according to SEQ ID NO:1, or a coding region of SEQ ID NO:1, said host being capable of increased production of cellulase, hemicellulase, other proteins involved in degradation of lignocellulosic material and/or other proteins as compared to the parental *Trichoderma reesei* strain.

3. The method according to claim 1, wherein the *Trichoderma reesei* host is genetically modified to be deficient of gene tre77513 having nucleotide sequence according to SEQ ID NO:1 or a coding region of SEQ ID NO:1, said host being capable of decreased production of cellulase, hemicellulase, other proteins involved in degradation of lignocellulosic material and/or other proteins as compared to the parental *Trichoderma reesei* strain.

4. A *Trichoderma reesei* host genetically modified to overexpress or to be deficient of gene tre77513 having nucleotide sequence according to SEQ ID NO:1 or a coding region of SEQ ID NO:1, said host being capable of increased or decreased production of cellulase, hemicellulase, other proteins involved in degradation of lignocellulosic material and/or other proteins as compared to the parental *Trichoderma reesei* strain.

5. The host according to claim 4, wherein the host is genetically modified to overexpress gene tre77513 having nucleotide sequence according to SEQ ID NO:1 or a coding region of SEQ ID NO:1, said host being capable of increased production of cellulase, hemicellulase, other proteins involved in degradation of lignocellulosic material and/or other proteins as compared to the parental *Trichoderma reesei* strain.

6. The host according to claim 4, wherein the host is genetically modified to be deficient of gene tre77513 having nucleotide sequence according to SEQ ID NO:1 or a coding region of SEQ ID NO:1, said host being capable of decreased production of cellulase, hemicellulase, other proteins involved in degradation of lignocellulosic material and/or other proteins as compared to the parental *Trichoderma reesei* strain.

7. A method for improved production or for producing an improved composition of proteins in a *Trichoderma reesei* host, said method comprising a step of cultivating the host of claim 4 under suitable culture conditions for protein production.

8. The method according to claim 7, wherein the protein is selected from the group consisting of cellulases, hemicellulases, side chain cleaving enzymes, lignocellulose degrading enzymes, pectinases, ligninases; amylolytic enzymes; proteases; invertases; phytases, phosphatases and hydrophobins.

9. The method according to claim 7, wherein the protein is a heterologous or a recombinant protein and expressed under a promoter of a gene encoding any one of the proteins whose production is affected by genetical modification of the host.

10. The method according to claim 9, wherein the promoter is a promoter of a gene encoding a cellulase, a hemicellulase, other protein involved in the degradation of lignocellulosic material or other secreted protein.

11. The method according to claim 9, wherein the promoter is a promoter of a gene encoding a protein selected from the group consisting of cellulases, hemicellulases, side chain cleaving enzymes, lignocellulose degrading enzymes, pectinases, ligninases; amylolytic enzymes; proteases; invertases; phytases, phosphatases and hydrophobins.

* * * * *

SEQUENCE LISTING

<160> NUMBER OF SEQ ID NOS: 18

<210> SEQ ID NO 1
<211> LENGTH: 2039
<212> TYPE: DNA
<213> ORGANISM: Trichoderma reesei

<400> SEQUENCE: 1

```
atgctgcgct actccccgt cttacacctg gatactctct ccttgccacc actgaccaat      60
gctcttcccc gcccaaagtg cgagtacctc agcgctgtcg atagctgcac gcactgccgc     120 gatgccacg tgcagtgcac tttcgacctg ccctggcgc gacgcggccc caaagcgagg       180
aagaagagcg accagcccgg ccagccgcct cctgatccga gctcgctctc caccgcggct     240
cgacccggcc agatgccgcc gccgctgacc ttctccggcc ccgcagtagc cgcgctgcag     300
cccttcgcct cgtcgtcgct gtcgcccgac gcggcctggg agcccgtcga gccgctcagc     360
attgacaacg gcctgccccg gcagccgctg gcgacctgc ccggcctctc caccatccag     420
aacatctcga cgcgccagcg atggatacac ctggccaacg ccatgacgct gcgcaacacg     480
acgctagagc gcgtctcgaa gcgatgtatc gacctcttct tcgactacct ctacccctc    540 accccctgg tgtacgagcc ggccctccgg gacgtgctcg catacatctt ctcccagccc    600
ttgcctggcg tcaaccaacc atcgccgctg tcacagctca cgccagaccc gaccaccggc    660
accacccccc tcaacgctgc cgagtcgtgg gccggctttg gccagcccag cggctcgcga    720
accgtcggca gcaggctggc tccctgggcc gactcgacct tcaccctggt cacggccgtc    780
tgcgcagagg cagcattcat gctacccaag gacattttcc ccgaaggaga atccgtctct    840
gagatcttgc tcgaagcctc tcgggactgc ctgcaccagc acctcgaggc cgacctggag    900
aatccgacgg ccaactcgat tgccattcgc tacttccact ccaactgcct ccacgctgcg    960
gggaagccca agtactcgtg gcacatattt ggcgaggcca tccgcctggc gcaggtcatg   1020
cagctgcacg aggaggctgc cctcgagggg ctcgtcccca tcgaggcaga gttccgccgt   1080
cgctgctttt ggatcctgta cttgggcgac aagtcagccg ctatactcaa caatcggccc   1140
atcaccatcc acaagtactg cttcgacgcc ggcatcacca cgctataccc gtcgggtatc   1200
gaggacgagt tcctgagcac ggcgtccgag ccgccccgga agagcttcat atccggcttc   1260
aacgcaaatg tgcggctctg gcagtccgcg gctgatttgc tgctggaaat ccgcgtgctg   1320
```

-continued

| | |
|---|---|
| caagatcaga tgatgcagca cttccgaggg accatgcccc cgaaccatgt gctgccctcc | 1380 |
| gccgacaggc agcatctcga ttctctctat gtccgcttca tcacctgctt ggacgatctc | 1440 |
| ccgccgtacc tccagtcgtg cactctggcg atggcagcga tggcagaagg caacgggtct | 1500 |
| gccgagtcca agcagtacgt gatacagtgc atcaacctgc aggtgacgtt tcactgtctg | 1560 |
| cgcatggtaa ttacgcagaa attcgaagac ctctcttatt ttgctcctgg cgttgagcag | 1620 |
| gctgatctca gaaagtcgga gattgtgcga gacatgctga gggtgatgaa cgaggcgccc | 1680 |
| ttttggggcc tgcaggccaa tggcgagcca aacgtgagtc gtttccttgt ctcttctctt | 1740 |
| ttctgcacac ccttttcttc gacgaccccc cctctctctt tatatccctg cggatatgta | 1800 |
| tatcatcaag cctcggcact tgttgctaat ctgtcctgat tatgttgtct ggatgctgca | 1860 |
| ggttgaaaag attcgcctta tcggagctag tttgctggcc atcatccatc gcaaccagga | 1920 |
| ttcacccttg gctacgcgag ccaggagcga cttttccgtg cttttggata ttctcacgcg | 1980 |
| gctggactcg aaggcgtcgg accaactgag gaatacgtcc actaccgttg ttggctaaa | 2039 |

<210> SEQ ID NO 2
<211> LENGTH: 2510
<212> TYPE: DNA
<213> ORGANISM: Trichoderma reesei
<400> SEQUENCE: 2

| | |
|---|---|
| atgggccggc aaccgagaca acgcccgatt tcgtgccact tgtgtagggt gcgcaagttg | 60 |
| cgctgcagcc gccagtttcc gtgttccaac tgcacgtctc gaggtgtcgt ctgccagcat | 120 |
| gaagggatcg cggtctcggc ggtctcggcg gcggcggcgg cggtgggagg acaacagcag | 180 |
| cagcagcagc agcagcagca gctcaagtct ccggctctga aggatgcgtc gacgctggag | 240 |
| ctgctggctc gtctggagcg gctggaaaac atcgtcgcag ctcaggggc cgggagggaa | 300 |
| ggcaaagacg cggacaactc cggctccggc ttcaacttca actccagcct caactccaac | 360 |
| tccaactcaa attttaactc caacttcaac cctagaaaag gggcagagac tcaagcagaa | 420 |
| cagagccgtc ccgtcacctc ccgcccggtg ccgcctagac tgcagcgctt gacagcggac | 480 |
| gcgctggagc ttgagcgatc ctgttccgac caaaagctga cggtgagccc gagcatcctc | 540 |
| tcctacccac gggcctgtct ctgcgcggta aggagtgctt tcgggatgag actgagactc | 600 |
| agcgcaggac tccttgatat ctgaacccat catcttccgt acctgtccca tacggctggc | 660 |
| cccaacgcag ccgtcctatg cttccaaaaa tggcctccca acgtccatgg ccgggccgat | 720 |
| ggacgccatc aagtgcatct ggctgcctcg gcgagatgag atgcgcatca tcctccaaaa | 780 |
| gtacatagct gatatctcct tgttctacca catcatccac gtccccacag tccagagcct | 840 |
| tgtcgaagac atttacgcag ggctggaggc aaacgttcgc gtcgacgtcg gcggcatcct | 900 |
| gctcctcctc agcatatgcg caagcacgac gtatgcctgg tcgcccctg acgatgtccg | 960 |
| gtgtctgttc tcggaccatg tcgaggcgaa tgcgcagtcc accttttgga tcaaggaggc | 1020 |
| gctggacgtc attgaccacg cgcagaggac ggcgcatgcg tcgttggaat gcatccaggg | 1080 |
| cctcatcatc ctgttctttg tcttttgtaa tcacgagagt gtgtcgttcc gtgcccgtag | 1140 |
| tgtcttcatg tcgccattg caatggcgac ggagctatcg ctgcatcgtc tcgacgatcc | 1200 |
| ccagggcagt cccatgggga cgcttcttcg gatgagcgag gccaagaagg agattgcaag | 1260 |
| gagagtgtgg tggttcatgg ttgcaacgga ctggtgagtc ggcgcccat atccatcaaa | 1320 |
| cattgttcaa gggcaagcc gccacccctct caaagcccct gtactgaccg actgcaggac | 1380 |
| acttgctcag ttcaactgtc cccaggaggg cttctacttc atccaccaga accagatggc | 1440 |

```
ggtcaacaag ccacggaatg caaacgacga ggacattatg gaaggcgtgg aaatcatcga      1500
tcggccagtc acagaggcga cctgcatctc ctactttgtc cagcgcatcc gcctggcaga      1560
ggtttgccgg acattgattg atcgggcacc cttgggcacg ccgacttcgg aaacctctgt      1620
gtacaagggt atactggaag tagacgcgaa gctcaaccag tttatgcggg aggccccgga      1680
cttcctttcc ctcgagtgtt ctcatctgga tagccttccc attaccgacc ccagacgctc      1740
gcctttcatc accgcgcagc gctacatgct gaatctgctt ctccaccggc agctgtgcaa      1800
gattcatctt ccttatctgg cccaagggac tgtcgatcct gcctatgcgt actcacgcga      1860
cgtttgcctg aggtcggcaa gggtggtctt tgagctcgat caccaactgc aaggagagtg      1920
cttgcccttc ttcaactccc gcctgaggtt ggccatggtt ttgcggagcc tgttcctggc      1980
tagtatcgcg ctcgtcttga acgcttgtct gacgggcgat gccgaggata ctggcgaggg      2040
agaagatgag atcgctggtg cgtggaagat attgcacgag gcacaaggcc aattccccccc     2100 ggcggcaaaa ctgctggagt tgtccatcca gattctcaga aagtataaga ttaagcatcg      2160
cgccctggat cttctgcaac agcaggtggc ggggatgtca ccttatggcg agacgtttcc      2220
gatgactccg gactcgacga atcacgatat gcgcatgagt acgatgcaac aacagaatgt      2280
aggtacgggc acgagtactg gcacaggcac aggcacaggc acaggcacag gcacaggcac      2340
aggcacaggc acaggcacag gcacaggcac gggaacaggg acatgcacaa gcgccgaacc      2400
ggacaatgtg ttgctggaac aacaatggca gatgctcgaa ggaaagatgg atctgaacac      2460
gatagattgg gataagttat tttggggtat tgatgccccg tttatataat                2510

<210> SEQ ID NO 3
<211> LENGTH: 994
<212> TYPE: DNA
<213> ORGANISM: Trichoderma reesei

<400> SEQUENCE: 3
atgctgagtc agagtcctcg agcaatgcag agctctcctg ccaacactgg cgcaaacacg        60
caagaacagc acttgcgcgc acagctcgag ctcctccaga accacgattc cgctgcctcg       120
tcagcctcgc ccacctcgag cgcgcgcgat ccccgaggcc ctccgtcgcg gcccccgaat       180
ggatacgacg ccctgccgcc tcaagacgtc gcccgccccc tcgccaagct agacgctgaa       240
gcgcacatcc accccgacct ccgcgcctcc gtcggcacg cgcccgccgc caacatgatg        300
cccatggtcc ctcccgccgg ccacagcccc ggtcccgccg ttccggggcc ctcagccgtg       360
ccgctggccc ccgcgccgcc gcagcagatg cccgtagacg actccaaccc agccgacggt       420
cgcaaggcga agcgcgagct gtcgcagtcc aagcgcgccg cccagaaccg agctgctcag       480
cgagctttcc gccagcgcaa ggagggctac atcaagaagc tcgagcagca ggttagagac       540
ctggccgatt tggagctctc gtacaagtcg atgcaatccg aaaactacgc gcttcgggaa       600
tacgtgatcc acctccaatc tcgactgctc gatacgcagg gcgaattccc gccgcctccc       660
cccaacgtga acctctcgca gccgtcgact gccgcgccgc ctccaccgac cgctcccgag       720
cagcaccacc agcagcaccc tcaccagcac cagcaacctc cgccgccgca gccgaccaac       780
agcagcaact cgggtgtcgg cacgcctctt gaggccgttg cgcaggccgt tgccggtctg       840
gccgcccagg aacagatggt tgagcgcgcg cagacgtacc ccagcccgcc cttcaaggcg       900
gaacagccag cgaacaggga tgccaactcc cgcgccgcga cagaagactt ggaaaggcca       960
atcaactctg aagcacggcc tggtcaatcc tagg                                  994
```

<210> SEQ ID NO 4
<211> LENGTH: 1459
<212> TYPE: DNA
<213> ORGANISM: Trichoderma reesei

<400> SEQUENCE: 4

```
atgacttctg aagcccccct caagacgtc gccgcccag aaggcactcc caatgccgcg      60
acaaacggcg ccgcaaacgg aaccgcatcg gagaagaaag agaggaaacc attctcatgg    120
gcgtaggttg atacacgaca aacccaacac catcttcaag gtgctaacac aatctgtcaa    180
gtcaaccgca tcccatcttc gtcatcgtcc tagtagggcc cgatgaggag ccctttggcc    240
tccagaagga cttcctctgt gaccgctccg aattctaccg caagtatttc gaggaaaatg    300
tcacagaaaa ggctctggag catattgtga aactcccaga tagcacgacc gaagtatttg    360
gcctcgtaca aagcttcctt tacaccggca agatcaatgg cgaaaactcc agcgtcactt    420
cctacgaatg cctggttggt ctctggaacc tgggtcacaa actcggcatc aagggggctat    480
gcgagcatac actagaggcc atggtggagt gccgacgaac cacgggccgg atcccagcga    540
cgccgcttct catccaggtc tggcgagaca cgcccgaggg atcgtctatt agagtcctct    600
tgctgtcttg ggctgctgag tacatgaggt cttcagacgc acgggcggag tttgccaagt    660
ctctaccgca ggaggtgctc agcgaactcg tggtgacgat gagctctttt gagacgacta    720
tactcccagc tccggctcct actgcacctg aactgtcac tggggccgcc gcccctgggc    780
tcccttcaag tgctatcagg tcgactcctg actctctttc ggcagggcca aggaagaatg    840
tccattacct agacgagcag cctgacgaag aagccctggg cgcaaagaag aatagacgat    900
ccattggctt tgcaagcgaa ccgagctcgg cccgcaagtc gcaccgcaag cctggctctt    960
ccccgccatt caaaccacag aagcgacgct cgagcgcagc catgttggag ggtaggacct   1020
tttcaactca gcagaagcta gacttttgtg ccgatctgct gaacaggatg ctctctgggc   1080
ccggtaagct ccccgatgct ctttgccttt atccccctgta catcagtcaa ctgactcaac   1140
ataggcttct ggacgcggct cgttggccct tttcgatcgc cagtcgaccc cgcggaagac   1200
ggcgtgccgg actactttga aaaggtcaag agaccaatgg acctcagcac agtgaagatg   1260
aagatggatc agaaggagta cgcgaccgag gaacagttcc ttggcgacgt gcggcagatt   1320
tttgaaaact gctttacgta ctggaagaag gcgatccga tgtgggcggc cggcgagagg   1380
ctgcagcgca cgtttgaaga aagtactcg cacatgaaca aatggatcgc caagctggga   1440
ggcgaagagg gcgagtagg                                                1459
```

<210> SEQ ID NO 5
<211> LENGTH: 3063
<212> TYPE: DNA
<213> ORGANISM: Trichoderma reesei

<400> SEQUENCE: 5

```
atgtccagat tctgtccgct ctgattgctt cagcctcacc agtttgtctc gttgcagaga     60
gcacgcgagc accttctact gtccggccgt ggcgcccgct ccatcgctac gccgctctct    120
acttacccac ctatatcgtc cgtgccgcaa atcatcatcg ccgacactga ttagcgagca    180
tcattccgcg acctcctgcg attcaacatc accatccatc gccggatacg aggcgcgatc    240
gtcgcagaca ggcgctatcc tgacggatat tgcgcttcgc aggcccatcc ttcaggaacc    300
agaccgccaa catgttgtga gtactggccg tcttttcttct ggtgccgggt cggtgtcttg    360
atcatgtctc cgtgactgac aaaaccggca gtgtcctacc accccctcca cgatatcccg    420
```

```
caggcgccta tggcgtcggc cttgggggcg tcgtccccct gatcgagacc aacaacacgt    480
tatcgaaccc gaccgggccc gaatatcagt tcctggtggg agagggtagg tcgaagccaa    540
tgcggccgcg caggttgcgt gtctcgggct gacggagcgg cgcataggaa catatgtcct    600
caaggaagac ctacacctgg ccacgccgcc gcctcatccc tccgaagcac cggtcgtcaa    660
tccgaacccg ctggccacga cgccgcagcc tgcgactgcg ggaaccaaga tgtccatatt    720
gagcctggag acgcgaccac ctcccttctt ctacaagggc ccggccgcca cgacgctgtc    780
actgggcggc accaccttga gcattcagga gcaccccagc gagggacgat actcgacgga    840 aggggggcaag agtagcgagg acggccgcgc aacgtcgagc gaggtaccga ccgggtccat    900
cacgctgggc tctgcgcccg cattcgggga gggcaactca ttgctggcgc cgactgtctc    960
caaggacgtg aacaagaaga agaagcctaa gaacaacgtg actaagagca actcgtcctt   1020
catttcgcgt gtaattgtta atgataacct cgcacggaag ctgacagaac ggccgtctga   1080
tggcctcttt gcttttgcca acatcaaccg ggcctttcag tggttagaca tgtcatcacc   1140
aaccaaggtg agctacagct acgcacaagg gattttttgt ggatttcgct ttggttcatc   1200
taacatcggt cgcagcaaga ttacttgaca aagattctct ttaccaaggc tcactgccta   1260
tgccatgacg tcaacatggt gaccaagagc gtttcgcata tcgacgtgat tatggggttt   1320
tccaccggcg aaatcatctg gtgggagccc atttcacagc gatatacccg tctcaacaag   1380
aacgtgagag caaatgtctc ttactgatca agtagacgca aagtccgcta acatccaagt   1440
agggaatcat caacaataca cccgtatccg aaatccgatg gatccctggt tccgagaatc   1500
tcttcctggc ggcgcatatg gatggtctgc tcgtggtgta cgacaaagag aaggaagacg   1560
ggcacctgaa tccggaggaa gagggattga atgctagtgt cagcggcagt gaaggcgagc   1620
tttcgaacgg ctcagcacac ggtaacggaa tcaggatcaa caagtcggtg cactccaaga   1680
atcaaaagac aaacccggta gccgcctgga agttgtccaa ccagcggatc aatgcctttg   1740
cctttccgcc cgacaaccgg catctggctg tagtgtcaga ggatgggacg ctgagggtca   1800
ttgactatct cagggaagag taagcaacgc tgccggcgcgt gtgatgatac cggcttgtgt   1860
cggcccgcta acagacggaa cagacttctg gatctatact actcctacta cggagggctg   1920
tcatgcgtct gctggacgcc agatggtaaa tacgtcctca ccggtggcca ggatgacttg   1980
atatccatat ggtcaatggc cgactcggcg cttgtcgccc gatgccaagg ccaccgatct   2040
tgggtatctg ccctggcatt cgacctttgg cgatgtgacg accgaagcta ccgctttggt   2100
agcgtgggag aagacggacg gctttgcctg tgggatttca gtgtgggcat gctgcaccgc   2160
ccaaagacag ccgtaagttg gcagacgtga cggtacactc acgctggaac gctcagctaa   2220
ccgttgccct ctacaactct tgcacaggcc ccggctcgcc atcgaggatc aatatcatca   2280
agaatcacgg ccccacacag aacggacacc aacacctcgg caaactcggg gggcatgggg   2340
ggtccgggca cggaagacga gtgggaggag aatgtgattg cacatcccgt gcagcccgt   2400 gccgtgatac cgatgctgcc tcctgttctg gtcagtataa cgagcaatgg caagccagcc   2460
ccgataacgt gcgtcaacta atccgaggct tcacagacac acgtgattga taaccatccc   2520
gcctgctggt tagcgtttac ggaagacgcc attatcacaa gctgcaaatc tggtaagttg   2580
tcagctctac atatctcttg tctgtatctt gatatcgttg aatctgtttc aattggctga   2640
cggaagcaaa ctgtacaggc catgttagaa cgtggagcag accaggcgtt caggcagcaa   2700
ctgcgtgagg cgatgatgag tgattgggca gatgaggtag gcgttacaag gcgcttctct   2760
```

```
acctaccgtc tttggtggtc tcttttgccc cctttctttc tatctcccgt tgaattgggc    2820
gggcgaggca tgtcttttg cctggtgttt agcctgggat ggctgctttg aacttttggg     2880
atttcgttct ggccttgtta ctattctgcg ctttttcaac tccaatatac ttctataccg    2940
gatgataagt tttgtgtggc ctcaccgacc aagacacgat tgtataagag ctgcccccgt    3000
catatgggtt cgtctcatga cggacactac atacaggtct actctgatac ggcctattga    3060
tgc                                                                  3063
```

```
<210> SEQ ID NO 6
<211> LENGTH: 25
<212> TYPE: DNA
<213> ORGANISM: Artificial sequence
<220> FEATURE:
<223> OTHER INFORMATION: chemically synthesized
<220> FEATURE:
<221> NAME/KEY: misc_feature
<222> LOCATION: (1)..(25)
<223> OTHER INFORMATION: 5' end primer: attB1 site

<400> SEQUENCE: 6
acaagtttgt acaaaaaagc aggct                                          25

<210> SEQ ID NO 7
<211> LENGTH: 37
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(37)
<223> OTHER INFORMATION: 5' end primer

<400> SEQUENCE: 7
ggggacaagt ttgtacaaaa aagcaggctt gcgcatc                             37

<210> SEQ ID NO 8
<211> LENGTH: 25
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(25)
<223> OTHER INFORMATION: 3' end primer: attB2 site

<400> SEQUENCE: 8
accactttgt acaagaaagc tgggt                                          25

<210> SEQ ID NO 9
<211> LENGTH: 59
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(59)
<223> OTHER INFORMATION: 5' end primer

<400> SEQUENCE: 9
ggggacaagt ttgtacaaaa aagcaggctt gcgcatcatg ctgcgctact cccccgtct     59

<210> SEQ ID NO 10
<211> LENGTH: 59
```

```
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(59)
<223> OTHER INFORMATION: 3' end primer

<400> SEQUENCE: 10
ggggacaagt ttgtacaaaa aagcaggctt gcgcatcatg ctgcgctact cccccgtct      59

<210> SEQ ID NO 11
<211> LENGTH: 59
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(59)
<223> OTHER INFORMATION: 5' end primer

<400> SEQUENCE: 11
ggggacaagt ttgtacaaaa aagcaggctt gcgcatcatg ggccggcaac cgagacaac      59

<210> SEQ ID NO 12
<211> LENGTH: 51
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(51)
<223> OTHER INFORMATION: 3' end primer

<400> SEQUENCE: 12
ggggaccact ttgtacaaga aagctgggta ttatataaac ggggcatcaa t              51

<210> SEQ ID NO 13
<211> LENGTH: 60
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(60)
<223> OTHER INFORMATION: 5' end primer

<400> SEQUENCE: 13
ggggacaagt ttgtacaaaa aagcaggctt gcgcatcatg ctgagtcaga gtcctcgagc     60

<210> SEQ ID NO 14
<211> LENGTH: 50
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(50)
<223> OTHER INFORMATION: 3' end primer

<400> SEQUENCE: 14
ggggaccact ttgtacaaga aagctgggtc ctaggattga ccaggccgtg                50

<210> SEQ ID NO 15
```

```
<211> LENGTH: 59
<212> TYPE: DNA
<213> ORGANISM: artificial sequene
<220> FEATURE:
<223> OTHER INFORMATION: chemically synthesized
<220> FEATURE:
<221> NAME/KEY: misc_feature
<222> LOCATION: (1)..(59)
<223> OTHER INFORMATION: 5' end primer

<400> SEQUENCE: 15
ggggacaagt tgtacaaaa aagcaggctt gcgcatcatg acttctgaag ccccctctc         59

<210> SEQ ID NO 16
<211> LENGTH: 50
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(50)
<223> OTHER INFORMATION: 3' end primer

<400> SEQUENCE: 16
ggggaccact tgtacaaga aagctgggtc ctactcgccc tcttcgcctc                   50

<210> SEQ ID NO 17
<211> LENGTH: 57
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(57)
<223> OTHER INFORMATION: 5' end primer

<400> SEQUENCE: 17
ggggacaagt tgtacaaaa aagcaggctt gcgcatcatg tccagattct gtccgct          57

<210> SEQ ID NO 18
<211> LENGTH: 51
<212> TYPE: DNA
<213> ORGANISM: artificial sequence
<220> FEATURE:
<223> OTHER INFORMATION: chemcially synthesized
<220> FEATURE:
<221> NAME/KEY: misc_feature
<222> LOCATION: (1)..(51)
<223> OTHER INFORMATION: 3' end primer

<400> SEQUENCE: 18
ggggaccact tgtacaaga aagctgggtg catcaatagg ccgtatcaga g                 51
```